US009480625B2

(12) United States Patent
McBean et al.

(10) Patent No.: US 9,480,625 B2
(45) Date of Patent: Nov. 1, 2016

(54) INFANT FEEDING SYSTEM

(71) Applicants: John M. McBean, Baltimore, MD (US); Kailas N. Narendran, Warwick, RI (US)

(72) Inventors: John M. McBean, Baltimore, MD (US); Kailas N. Narendran, Warwick, RI (US)

( * ) Notice: Subject to any disclaimer, the term of this patent is extended or adjusted under 35 U.S.C. 154(b) by 0 days.

(21) Appl. No.: 14/861,372

(22) Filed: Sep. 22, 2015

(65) Prior Publication Data
US 2016/0015603 A1   Jan. 21, 2016

Related U.S. Application Data

(63) Continuation of application No. 13/854,054, filed on Mar. 30, 2013, now Pat. No. 9,161,887.

(60) Provisional application No. 61/712,527, filed on Oct. 11, 2012.

(51) Int. Cl.
| | |
|---|---|
| B65B 37/06 | (2006.01) |
| A61J 9/00 | (2006.01) |
| A61J 11/04 | (2006.01) |
| A61M 1/06 | (2006.01) |
| A61J 9/06 | (2006.01) |
| B65B 3/17 | (2006.01) |
| B65B 7/28 | (2006.01) |
| A61J 9/08 | (2006.01) |

(52) U.S. Cl.
CPC ............... *A61J 9/005* (2013.01); *A61J 9/001* (2013.01); *A61J 9/06* (2013.01); *A61J 11/04* (2013.01); *A61M 1/06* (2013.01); *A61M 1/062* (2014.02); *B65B 3/17* (2013.01); *B65B 7/2835* (2013.01); *B65B 37/06* (2013.01); *A61J 9/085* (2013.01)

(58) Field of Classification Search
CPC ............ A61J 9/005; A61J 9/001; A61J 9/06; A61J 9/085; A61M 1/061; A61M 1/06; A65B 7/2835; A65B 3/17; A65B 3/06
See application file for complete search history.

(56) References Cited

U.S. PATENT DOCUMENTS

| | | |
|---|---|---|
| 3,549,036 A | 12/1970 | Ritsi |
| 4,895,264 A | 1/1990 | Phlaphongphanich |
| 5,024,341 A | 6/1991 | Dekerle |
| 5,188,266 A | 2/1993 | Loulias |
| 6,991,121 B1 | 1/2006 | Kipperman et al. |

(Continued)

OTHER PUBLICATIONS

International Searching Authority, International Application No. PCT/US2013/064456, dated Jan. 13, 2014, together with the Written Opinion of the International Searching Authority, 17 pages.

(Continued)

*Primary Examiner* — Erik Kashnikow
*Assistant Examiner* — Chaim Smith
(74) *Attorney, Agent, or Firm* — Sunstein Kann Murphy & Timbers LLP

(57) ABSTRACT

A method of feeding breast milk to an infant includes providing a spout pouch having a spout, providing a plurality of adapters configured to couple to the spout pouch, coupling the spout of the spout pouch to a first adapter, coupling the first adapter to a breast pump, operating the breast pump to express breast milk into the spout pouch, so that the spout pouch collects the expressed breast milk, coupling a second adapter to the spout of the spout pouch, and coupling the second adapter to a nipple, so that expressed breast milk flows from the spout pouch to the nipple. Other systems, methods, and components are also provided.

16 Claims, 23 Drawing Sheets

(56) References Cited

U.S. PATENT DOCUMENTS

| | | |
|---|---|---|
| 7,185,775 B1 | 3/2007 | Decal |
| 7,287,657 B1 | 10/2007 | Rodriguez |
| 8,992,084 B2 | 3/2015 | Pellingra et al. |
| 9,161,887 B2 | 10/2015 | McBean et al. |
| 2006/0011497 A1 | 1/2006 | Segovia, Jr. et al. |
| 2007/0095778 A1 | 5/2007 | Catton |
| 2007/0280565 A1 | 12/2007 | Lyon et al. |
| 2010/0215294 A1 | 8/2010 | Berman |
| 2010/0258519 A1 | 10/2010 | Shelby |
| 2011/0151069 A1* | 6/2011 | Harding ............... A61J 9/001 426/117 |
| 2011/0240587 A1 | 10/2011 | Cohn |
| 2014/0124469 A1 | 5/2014 | Richard |
| 2015/0024085 A1 | 1/2015 | McBean et al. |

OTHER PUBLICATIONS

European Patent Office, Extended European Search Report—Application No. 13846217.1 dated May 13, 2016, 7 pages.

\* cited by examiner

INFANT FEEDING SYSTEM

CROSS REFERENCE TO RELATED APPLICATIONS

The present application is a continuation application of U.S. patent application Ser. No. 13/854,054 filed on Mar. 30, 2013, which claims the benefit of U.S. Provisional Patent Application No. 61/712,527 filed Oct. 11, 2012, the disclosures of which are incorporated by reference herein in their entirety.

TECHNICAL FIELD

The present invention relates to feeding systems, and more particularly to a nipple and infant feeding system.

BACKGROUND ART

Traditionally, baby feeders have taken the form of a generally cylindrical bottle (typically, glass or plastic) and a removable nipple closing one end of the bottle. The nipple is commonly secured to the bottle by a threaded circular ring or collar having a central hole through which the nipple protrudes and which holds it securely to the bottle. An example is U.S. Pat. No. 8,113,364, issued Feb. 14, 2012 to Ladan Asadi.

In some feeders using rings or collars to secure the nipple, flexible liners are inserted inside a rigid bottle to hold the liquid contents. An example is U.S. Pat. No. 6,616,000, issued Sep. 9, 2003 to Charles Renz and assigned to Playtex Products, Inc.

Some baby feeders attach a removable nipple directly to a disposable feeder body. An example is U.S. Patent Application Pub. No.2012/0234790 A1.

Many kinds of flexible, reclosable bags are known and used for food storage, including liquid foods, and some of these are used for receiving storing breast milk. One example is the Medela™ "pump and save"™ breastmilk bag. This bag is essentially a flat pouch closed on three sides but having a throat or opening extending the width of the bag on the top side through which the bag may be filled when opened. The bag is closed by forcing a rib along the top into a corresponding channel to form a friction seal. A separate feeder bottle is required for subsequent feeding of the contents.

These systems all require significant handling during milk collection, storage, and preparation for feeding, and can unnecessarily expose the contents to contamination.

SUMMARY OF THE EMBODIMENTS

In one embodiment of the invention, a method of feeding breast milk to an infant includes providing a spout pouch having a spout, providing a plurality of adapters configured to couple to the spout pouch, coupling the spout of the spout pouch to a first adapter, coupling the first adapter to a breast pump, operating the breast pump to express breast milk into the spout pouch, so that the spout pouch collects the expressed breast milk, coupling a second adapter to the spout of the spout pouch, and coupling the second adapter to a nipple, so that expressed breast milk flows from the spout pouch to the nipple.

In related embodiments, the first adapter may have a first threaded end configured to mate with threads on the spout and a second threaded end configured to mate with threads on the breast pump. The method may further include inserting the spout pouch into a holder, the holder having a top and a body, the top of the holder has an opening configured to removably receive and secure the spout and the body is configured to receive at least a portion of the spout pouch. The opening of the holder may be C-shaped and configured to laterally receive the spout. The spout may be configured to couple to the opening in the holder with a snap fit. The second adapter may have a first threaded end configured to mate with threads on the spout and a second threaded end configured to mate with threads on the nipple or a nipple component.

In another embodiment of the invention, a method of feeding breast milk to an infant includes providing a spout pouch having a spout, coupling the spout of the spout pouch to an adapter, coupling the adapter to a breast pump, operating the breast pump to express breast milk into the spout pouch, so that the spout pouch collects the expressed breast milk, removing the breast pump, and coupling the adapter to a nipple, so that expressed breast milk flows from the spout pouch to the nipple.

In related embodiments, the adapter may have a first threaded end configured to mate with threads on the spout and a second threaded end configured to mate with threads on the breast pump. The method may further include inserting the spout pouch into a holder, the holder having a top and a body, the top of the holder has an opening configured to removably receive and secure the spout and the body is configured to receive at least a portion of the spout pouch. The opening may be C-shaped and configured to laterally receive the spout. The spout may be configured to couple to the opening in the holder with a snap fit. The adapter may have a first threaded end configured to mate with threads on the spout and a second threaded end configured to mate with threads on the nipple or a nipple component.

In another embodiment of the invention, an infant feeding system includes a nipple, at least one spout pouch having a spout, a set of adapters, at least one adapter configured to couple to the nipple and to the spout and at least another adapter configured to couple to a breast pump and to the spout, and a holder having a top and a body, the top of the holder has an opening configured to removably receive and secure the spout and the body is configured to receive at least a portion of the spout pouch.

In related embodiments, the adapter configured to couple to the breast pump may have a first threaded end configured to mate with threads on the spout and a second threaded end configured to mate with threads on the breast pump. The opening in the holder may be C-shaped and configured to laterally receive the spout. The spout may be configured to couple to the opening in the holder with a snap fit. The adapter configured to couple to the nipple may have a first threaded end configured to mate with threads on the spout and a second threaded end configured to mate with threads on the nipple or a nipple component.

In another embodiment of the invention, an infant feeding system includes a nipple, at least one spout pouch having a spout, at least one adapter having a first end configured to couple to the spout and having a second end configured to couple to the nipple and configured to couple to a breast pump, and a holder having a top and a body, the top of the holder has an opening configured to removably receive and secure the spout and the body is configured to receive at least a portion of the spout pouch.

In related embodiments, the second end of the adapter may have a threaded end configured to mate with threads on the breast pump and configured to mate with threads on the nipple or a nipple component. The opening in the holder may be C-shaped and configured to laterally receive the spout. The spout may be configured to couple to the opening in the holder with a snap fit. The first end of the adapter has a threaded end configured to mate with threads on the spout.

In one embodiment of the invention, a method of collecting expressed breast milk for later feeding to an infant includes providing a spout pouch, the spout pouch having a spout, coupling the spout of the spout pouch to a breast pump, and operating the breast pump to express breast milk into the spout pouch, so that the spout pouch collects the expressed breast milk.

In related embodiments, coupling the spout of the spout pouch to the breast pump may include coupling an adaptor to the spout. The adaptor may have a threaded end configured to mate with threads on the breast pump. The method may further include inserting the spout pouch into a holder. The holder has a top and a body, and the top of the holder has an opening configured to removably receive and secure the spout and the body has an interior configured to receive the spout pouch.

In another embodiment of the invention, a method of feeding a liquid to an infant includes providing the liquid in a spout pouch, the spout pouch having a spout, and coupling a nipple to the spout of the spout pouch.

In related embodiments, coupling the nipple may include coupling the nipple in a manner that requires no other hardware. The nipple may include a connector having an axial bore that is coupled to an orifice in the nipple, the connector may form a liquid tight seal with the spout of the spout pouch, and coupling the nipple to the spout may include inserting the connector into the spout. The connector may have an inlet region and the inlet region further includes a circumferentially disposed flange, the spout may include a feature configured to receive the flange, and coupling the nipple to the spout may include inserting the connector into the spout until the flange has engaged with the feature. The feature may be a recess or a ridge in the spout. The method may further include inserting the spout pouch into a holder, the holder having a top and a body, wherein the top of the holder has an opening configured to removably receive and secure the spout and the body has an interior configured to receive the spout pouch. The opening may be C-shaped and may be configured to laterally receive the spout. The body may have at least one opening configured to allow the insertion of the spout pouch into the interior of the body, wherein the at least one opening is disposed in a location opposite the top or on a side of the body.

In another embodiment of the invention, a nipple formed of a deformable material includes a connector configured to be coupled to a container of liquid. The container has an opening, the connector includes a connector region configured to engage with the opening of the container so as to form a liquid tight seal with the opening without need for additional hardware, and the connector includes an axial bore. The nipple further includes a tip region configured to be placed in a mouth of an infant. The tip region has an orifice in communication with the axial bore, so that the liquid can flow from the container through the axial bore and the orifice into the mouth of the infant.

In related embodiments, the orifice may be a slit. The nipple may have a longitudinal axis that is aligned with the axial bore and the nipple may further include a skirt that generally surrounds the connector, the skirt having a bottom end that has an oblong shape, the oblong shape having a long axis that is transverse to the longitudinal axis. The nipple may further include a skirt having a lower region that generally surrounds the connector and an abutment region that abuts the tip region, wherein the abutment region has a stiffness greater than a stiffness of the lower region. The skirt may include a shoulder between the abutment region and the lower region. The slit may have a length and a slit axis along the length, and wherein the long axis of the oblong shape of the skirt is transverse to the slit axis. The nipple may have a longitudinal axis that is aligned with the axial bore and the nipple may further include a skirt that generally surrounds the connector, the skirt having a bottom end that has an oblong shape, the oblong shape having a long axis that is transverse to the longitudinal axis. The connector may have an inlet region and the inlet region may further include a circumferentially disposed flange configured to secure the connector to the opening. The container may be a spout pouch having a spout, and the spout defines the opening of the container, and the spout may include a feature configured to receive the flange.

In related embodiments, a nipple system includes a nipple, as described above, a nipple cover configured to cover the nipple, and a base configured to removably inter-engage with the nipple cover when the nipple cover covers the nipple, so that the nipple cover and the inter-engaged base form a case for the nipple.

In related embodiments, an infant feeding system includes a nipple, as described above, and a spout pouch having a spout, wherein the connector of the nipple is configured to engage with the spout so as to form a liquid tight seal with the spout without need for additional hardware.

In related embodiments, the infant feeding system may further include a holder having a top and a body, wherein the top of the holder has an opening configured to removably receive and secure the spout and the body has an interior configured to receive the spout pouch. The infant feeding system may further include a nipple cover configured to cover the nipple. The nipple cover may be further configured to releasably engage with the nipple. The infant feeding system may further include a threaded cap configured to cover the spout, wherein the spout includes threads configured to mate with the threaded cap.

In another embodiment of the invention, a nipple formed of a deformable material includes a skirt having a bottom end with an oblong shape that has a long axis, a securing flange coupled to the bottom end of the skirt, the securing flange configured to be secured to a container of liquid, and a tip region configured to be placed in a mouth of an infant. The tip region has an orifice that allows the liquid to flow from the container into the mouth of the infant, wherein the orifice is a slit having a length and a slit axis along the length, and wherein the long axis of the oblong shape of the skirt is transverse to the slit axis.

In related embodiments, an infant feeding system includes a nipple, as described above, and an engagement ring configured to secure the securing flange to a container that holds liquid, so that the liquid is allowed to flow from the container into a mouth of an infant.

In another embodiment, an infant feeding system includes a nipple, as described above, and a nipple adapter configured to secure the nipple to a container that holds liquid, so that the liquid is allowed to flow from the container into a mouth of an infant. The infant feeding system may further include a nipple cover configured to cover the nipple.

BRIEF DESCRIPTION OF THE DRAWINGS

The foregoing features of embodiments will be more readily understood by reference to the following detailed description, taken with reference to the accompanying drawings, in which:

FIG. 15a shows a perspective view of the bottom, FIGS. 15b and 15c show side front and side views, respectively, and FIG. 15d shows a top view of the one-piece feeding nipple. FIG. 15d shows a slit at the tip of the nipple, through which the pouch contents pass into the infant's mouth.

DETAILED DESCRIPTION OF SPECIFIC EMBODIMENTS

Definitions. As used in this description and the accompanying claims, the following terms shall have the meanings indicated, unless the context otherwise requires:

A "spout pouch" is a flexible pouch to which is affixed a spout that is configured to receive a cap; the cap alone can be coupled, without use of other hardware, to the spout of the spout pouch.

A "cap" for a spout pouch is a single-piece component.

A spout that is "substantially rigid" is a spout that retains shape sufficiently so that the spout can be readily coupled to another member, to form a liquid tight seal, without use of any additional hardware.

A "liquid" includes any of breast milk, formula, milk, juice, and pureed food.

"Expressed breast milk" includes breast milk that has been pumped, collected extracted or gathered.

A "nipple" is a feeding appliance for an infant, wherein a portion of the appliance is coupled to a container of liquid and a tip region of the appliance is configured to be placed in a mouth of the infant so that the liquid can flow from the container into the mouth of the infant.

An "orifice" in a nipple includes a slit, a hole, or a combination of both, through which liquid emerges into the mouth of an infant using the nipple to ingest the liquid.

A "slit" in a nipple is an orifice created without the removal of material in the nipple, so that opposing walls of the nipple defining the slit are in contact with one another over their entire length when the nipple is not deformed. For example, a slit is formed when a knife is used to pierce through a layer of material, and is moved through the material, cutting the material but not removing any material from the original shape. A slit may be straight or curved.

Figure 1:
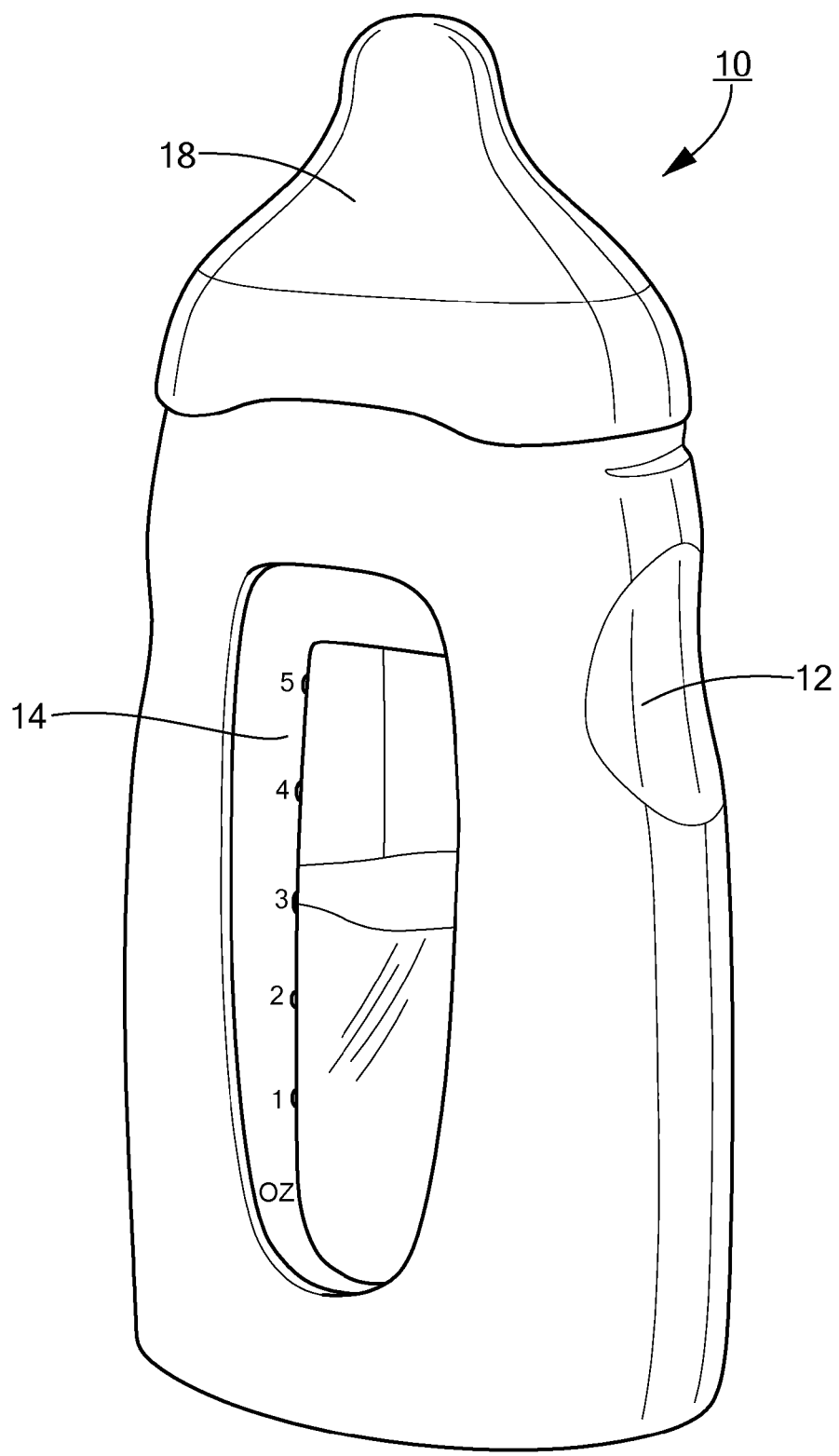
FIG. 1 is a perspective view of an assembled infant feeding system including a holder, spout pouch, nipple (not visible), and nipple cover according to embodiments of the present invention.

FIG. 1 is a perspective view of an assembled infant feeding system 10. The infant feeding system 10 may include a holder 12, a spout pouch 14, a nipple 16 (shown in FIG. 2), and a cover 18. In one embodiment of the invention, the spout pouch 14 snaps into the holder 12. A rigid spout 20 (described in more detail below) snaps into a feature on the holder 12, after being forced through a narrow gap in the holder 12. The spout pouch 14 may be inserted into the holder 12 by passing through openings either in the bottom, sides, front, and/or back of the holder 12. The cover 18, which also serves as the top of a nipple case (shown and described in more detail below in FIG. 7), attaches to the nipple 16 (which is inserted into the spout of the spout pouch), or it may attach to the holder 12. The cover 18 may be coupled to the nipple 16 or holder 12 by any of a friction fit, a snap fit, a magnetic coupling, a connection that requires a twisting action, or other type of connection.

Figure 2:
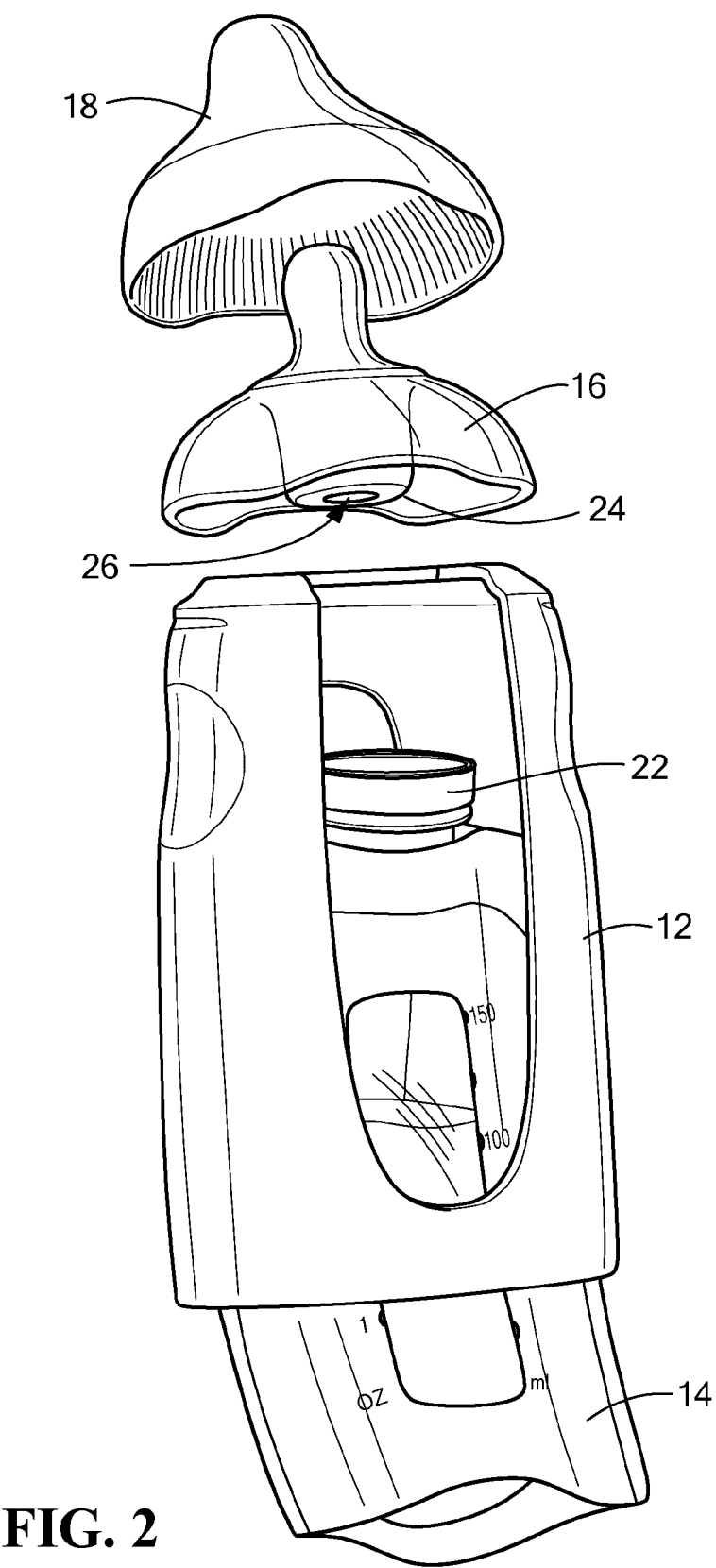
FIG. 2 is an exploded view of an infant feeding system with a spout pouch (with cap) being assembled into a holder, along with a nipple and nipple cover according to embodiments of the present invention.

FIG. 2 is an exploded view of the infant feeding system 10 with the spout pouch 14 and cap 22 being assembled into the holder 12, and a nipple 16 and nipple cover 18. The spout pouch 14 has a spout 20 that is configured to snap fit into the holder 12. The holder 12 may be a thin-walled plastic shell, designed to hold the generally rigid spout 20 of the spout pouch 14. The connection between the spout 20 and holder 12 may be any of a friction fit, a snap fit, a magnetic coupling, a connection that requires a twisting action, or other type of connection. On one embodiment, the nipple 16 is oblong in shape, for the purpose of a more ergonomic connection with an infant's mouth. The nipple 16 connects to the spout 20 of the spout pouch 14 by a connector 24 (shown in more detail in FIGS. 15a-15d) on the bottom of the nipple 16. The connector 24 has a hollow bore 26, through which liquids, foods, pastes, or gels pass from the pouch into the infant's mouth. In use, the connector 24 is pushed into the opening of the spout 20, creating a liquid-tight connection between the connector 24 and the spout 20. The connector 24 may be slightly larger in size than the opening of the spout 20, but the connector 24 may be made of a compressible material, so it may be forced into the opening of the spout 20. In one embodiment, the nipple 16 is a single piece, made of a single material.

Figure 3:
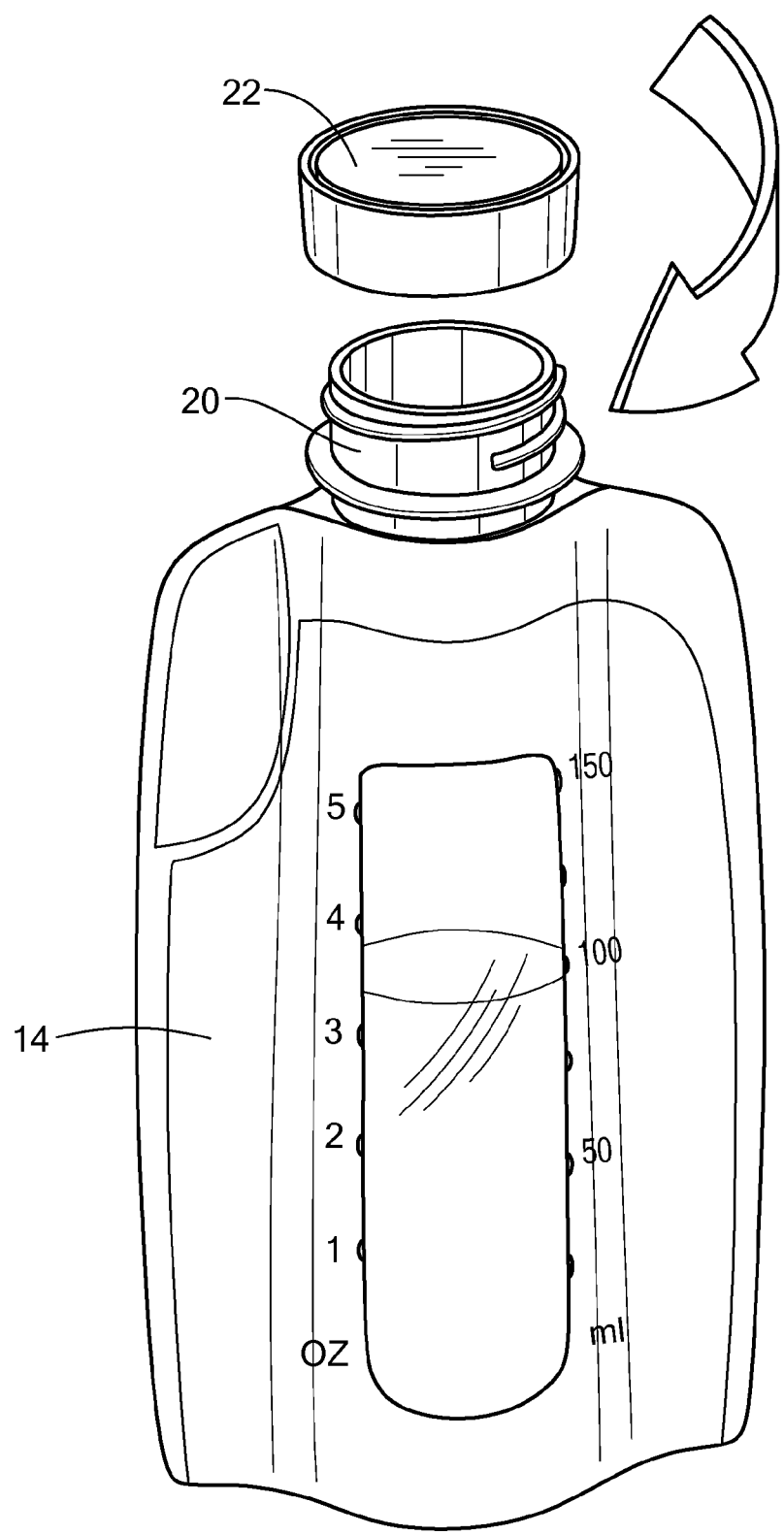
FIG. 3 is a perspective view of a cap being assembled on to a spout pouch according to embodiments of the present invention.

FIG. 3 is a perspective view of a cap 22 being assembled on to a spout pouch 14. The spout 20 of the spout pouch 14 may be made of a generally rigid material, and is configured to receive a cap 22 capable of forming a water tight seal. In one embodiment, the cap 22 may be threaded, having helical features which interact with features on the spout 20, causing the cap 22 to form a liquid-tight seal with the spout when the cap 22 is twisted relative to the spout 20. In other embodiments, the cap 22 may be pressed, pulled, or twisted into place onto the spout 20. In other embodiments, the connection between the cap 22 and spout 20 may be an interference fit (e.g., where two or more elements are forced together, causing the materials to deform at their interface), a friction fit (e.g., where the cap is held to the spout by friction), a snap fit, or a latch fit (e.g., where a pressing, pulling, twisting action is required to secure the cap to the spout). In one embodiment, the pouch 14 material is a thin, flexible plastic film, and the spout 20 is a thicker, more rigid plastic material.

Figure 4:
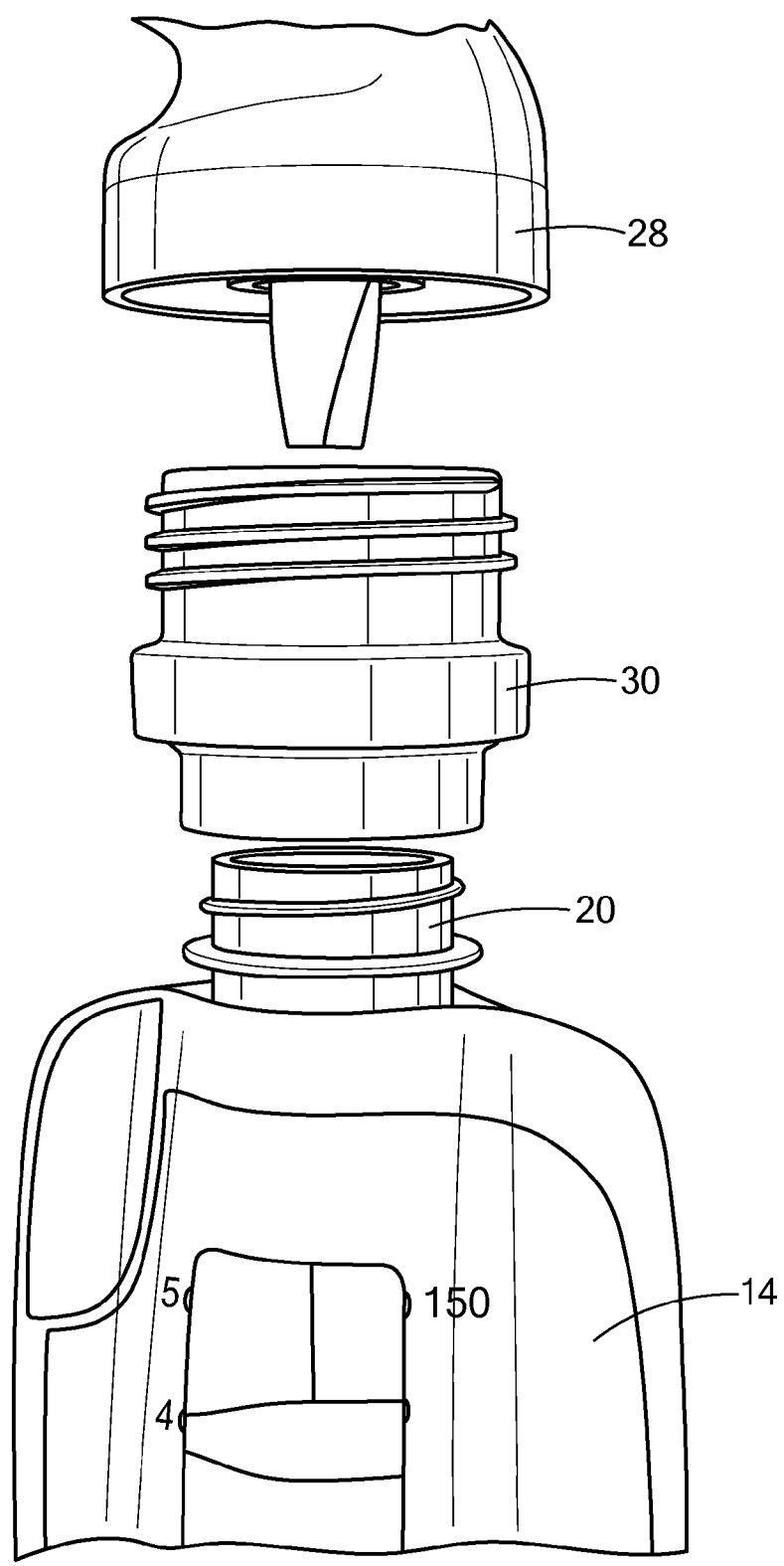
FIG. 4 is an exploded, perspective view of a spout pouch being connected to a breast pump, using a threaded adapter, according to embodiments of the present invention.
Figure 5:
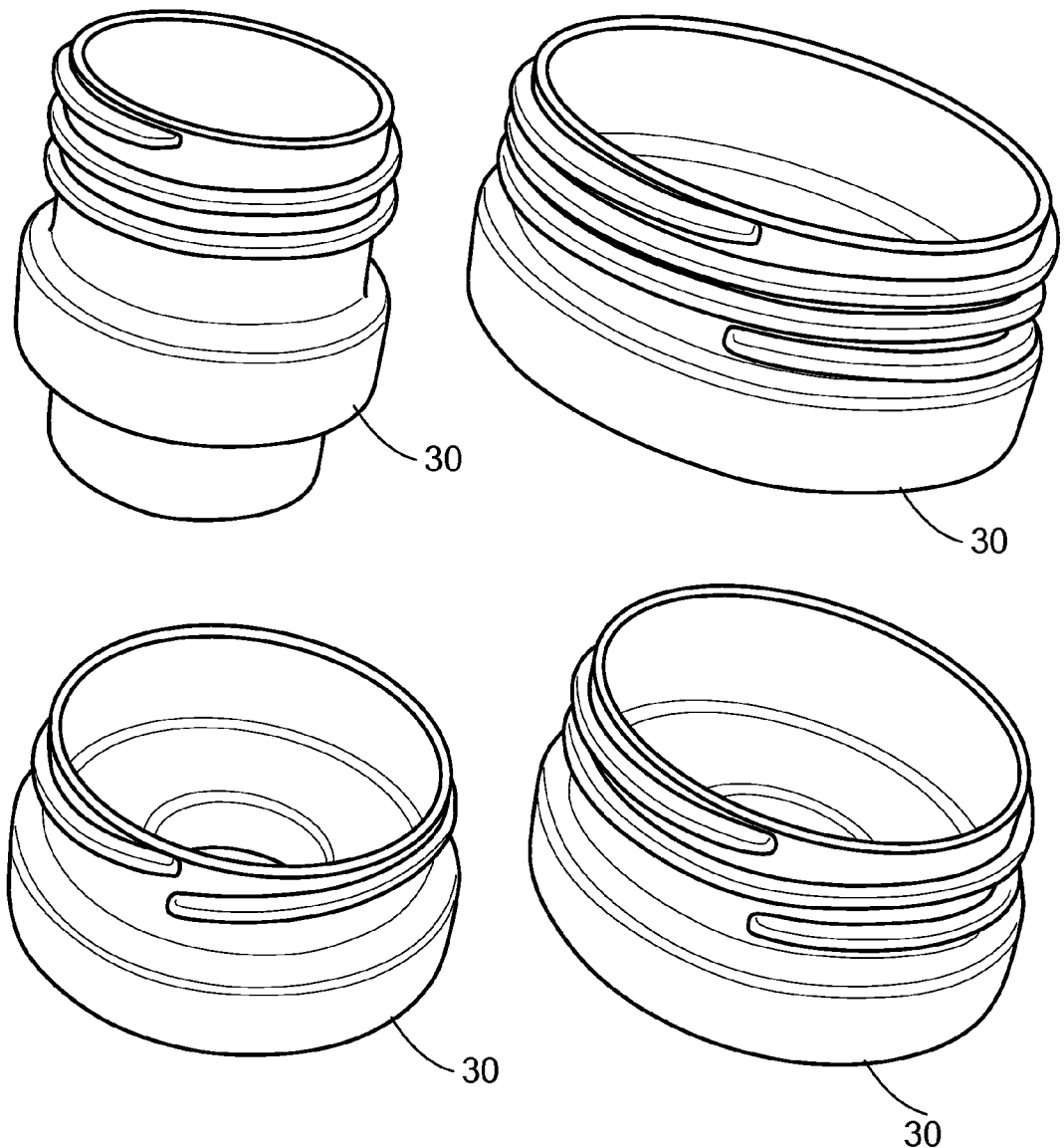
FIG. 5 is a perspective view of multiple adapters which may be used to couple a spout pouch to various breast pumps, for collecting breast milk, according to embodiments of the present invention. Additionally, these adapters may be used to couple feeding nipples to spout pouches, for the purpose of feeding an infant, according to embodiments of the present invention.

FIG. 4 is an exploded, perspective view of a spout pouch 14 being connected to one end of a breast pump 28, using a threaded adapter 30. In use, the adapter is coupled to the spout 20 of the spout pouch 14, and the end of the breast pump 28 is coupled to the adapter 30. The breast pump is then operated to express breast milk into the spout pouch 14 so that the spout pouch 14 collects the expressed breast milk. In one embodiment, the spout pouch 14 is configured to receive the breast milk that is pumped from a woman's breast by a breast pump. In order to attach to multiple different pumps available on the market, various types of adapters, such as shown in FIG. 5, may be provided to couple the spout 20 of the spout pouch 14 to the end of a breast pump 28. In one embodiment, the adapter 30 is coupled to the spout 20 of the spout pouch 14 by a threaded connection, and the other side of the adapter is coupled to the outlet of a breast pump 28 by a threaded connection. In other embodiments, the connection between adapter 30 and spout pouch 14 may be any of an interference fit, a friction fit, a snap fit, or a latch fit. Similarly, the connection between adapter and breast pump may be any of an interference fit, a friction fit, a snap fit, or a latch fit. Connecting the adapter 30 to the end of the breast pump 28, or connecting the adapter 30 to the spout 20 of the spout pouch 14 may require any of (or any combination of) twisting, pushing, pulling, or squeezing. In yet another embodiment, the spout 20 may couple directly to the outlet of a breast pump 28, by any of the means listed above, without the need for an adapter. In some embodiments, the spout pouch 14 may be held in a holder 12 while the spout pouch 14 is coupled to the adapter, or to a breast pump, or both. A holder 12 may be used to provide a stable base for holding the spout pouch 14 during and after collecting milk using a breast pump. The holder 12, and its connection to the spout pouch 14, are described further below.

FIG. 5 shows multiple adapters which may be used to couple spout pouches 14 to breast pumps, for collecting breast milk in accordance with embodiments of the present invention. Additionally, these adapters 30 may be used to couple feeding nipples to spout pouches, for the purpose of feeding an infant. Since there are multiple different brands of breast pumps, there are many different types of connections required to couple the spout pouches 14 to the outlets 28 of a variety of breast pumps available on the market. Different adapters may be provided, with different types of connections, for coupling to a wide range of breast pumps for collection of pumped breast milk. These connections may include any of a threaded connection, an interference fit, a friction fit, a snap fit, or a latch fit. The other side of the adapter is coupled to the spout of the spout pouch, to allow liquid to flow into the pouch. The types of connections between the adapter and the nipple may be any of the connection types listed above. Typically, the connection between the adapter and the nipple will be a threaded connection. In some cases, the adapter 30 used to couple a breast pump to the spout pouch may be the same adapter that is used to couple a feeding nipple to the spout pouch. In some embodiments, an infant can be fed using only the spout pouch 14 and a nipple 16. In other embodiments, a spout pouch, an adapter, and a nipple may be used. In yet another embodiment, a holder 12 may be used to hold the spout pouch during feeding, in conjunction with either an adapter and a nipple or a nipple alone.

Figure 6:
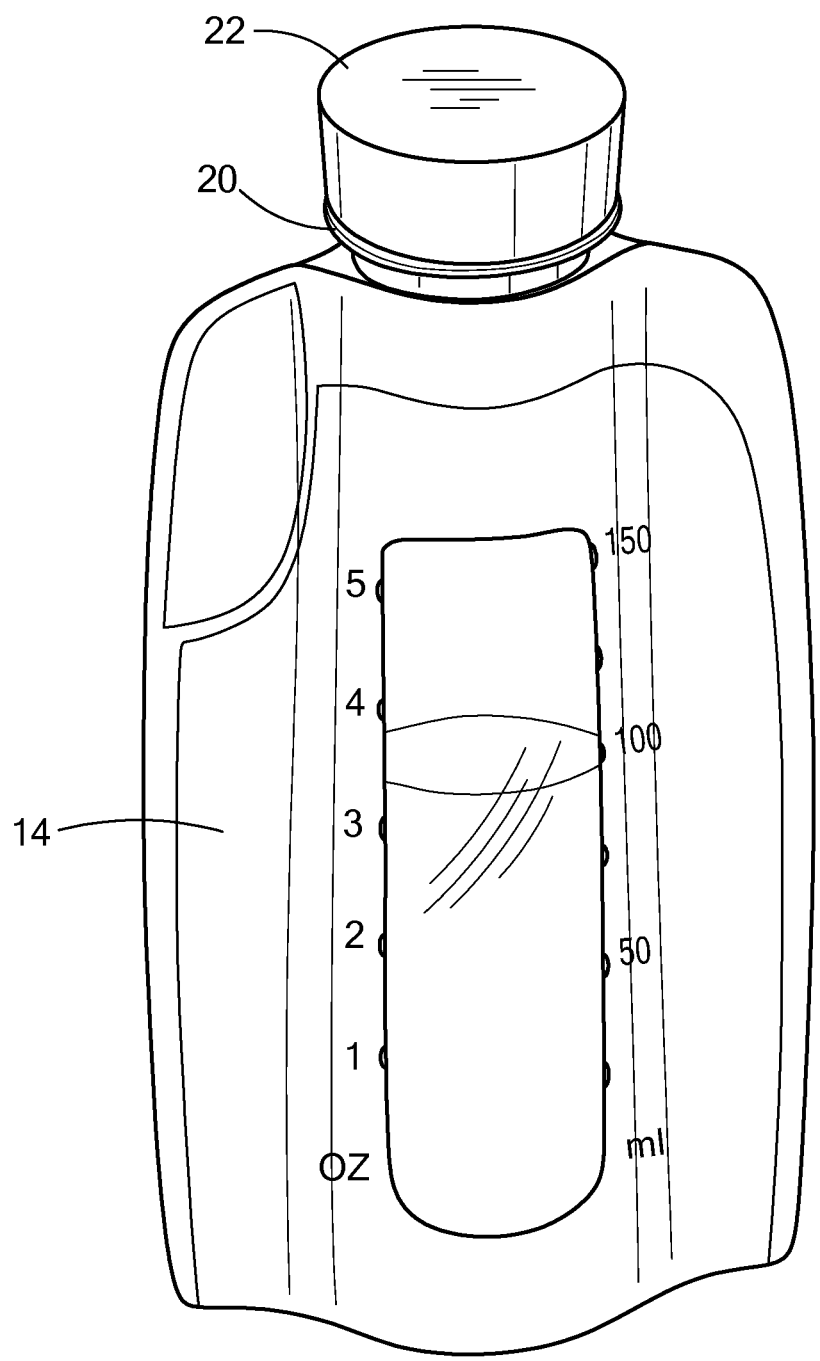
FIG. 6 is a perspective view of a spout pouch with a cap assembled to form a liquid tight seal according to embodiments of the present invention.

FIG. 6 shows a spout pouch 14 with cap 22 assembled to form a liquid tight seal in accordance with embodiments of the present invention. The spout is coupled to the pouch to form a liquid-tight vessel, designed for holding liquids or foods for infant feeding. An infant may feed directly from the pouch, either by passing the liquid from the pouch, through the spout into the infant's mouth (directly or indirectly), or the pouch may be used for storage only, and the contents may be transferred to another container for feeding. For direct feeding, different feeding devices may be used in conjunction with the spout pouch. Various nipples, valves and other devices for interfacing with an infant's mouth may be connected to the spout of the spout pouch. Various types of connections may be used for coupling these feeding devices to the spout. Examples of such connections are: threaded connections, an interference fit (e.g., where two or more elements are forced together, causing the materials to deform at their interface), a friction fit (e.g., where the feeding device is held to the spout by friction), a snap fit, or a latch fit (e.g., where a pressing, pulling, twisting action is required to secure the feeding device to the spout. Examples of feeding devices are: nipples, perforated containers, openings, and valves. Optionally, an infant or child could feed directly from the pouch without a feeding device attached—the infant or child could simply pour or suck the contents of the pouch through the pouch and into his or her mouth. Similarly, a spoon, a fork, a straw, or other utensil may be passed through the spout in order to pick up and remove contents of the pouch for feeding. The connection between the cap and spout may be any of the types of connections listed previously.

Figure 7:
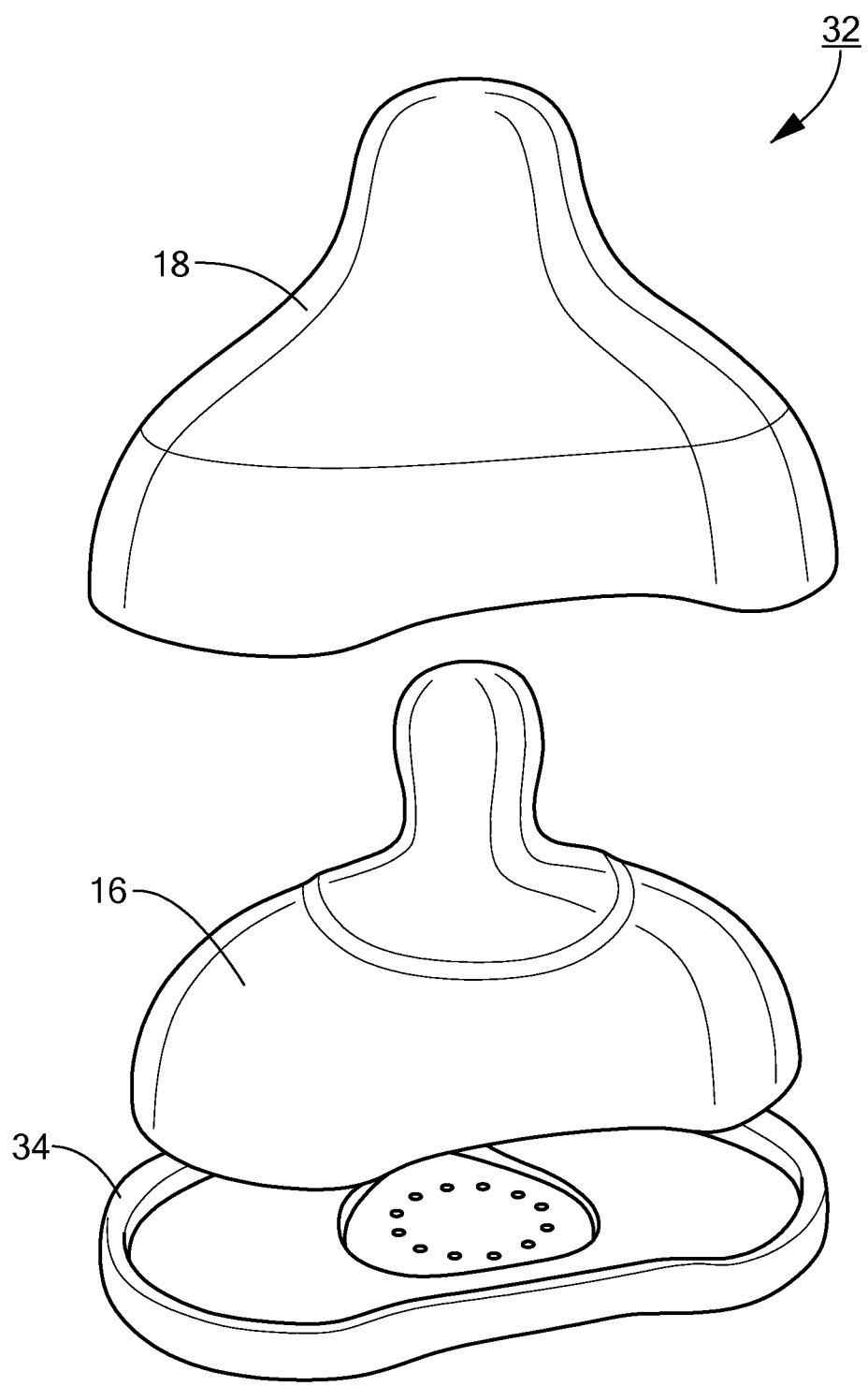
FIG. 7 is an exploded perspective view showing a feeding nipple inside its case, according to embodiments of the present invention. The top of the case is a cover for the nipple and holder, when the nipple is removably coupled to the spout pouch, and the spout pouch is removably coupled to the holder.

FIG. 7 is an exploded view showing a feeding nipple inside its case 32 in accordance with embodiments of the present invention. The infant nipple case 32 includes a nipple cover 18 and a base 34 that cover and protect a nipple 16. The case 32 components serve three purposes. 1) The nipple cover 18 and base 34 of the case 32 combine to form a protective case for the nipple 16; 2) The nipple cover 18 of the case can be used as a cover for the nipple 16 when the nipple 16 is assembled to the spout pouch 14, and the spout pouch 14 is assembled to the holder 12; and 3) the nipple cover 18 of the case can be used as a tool to push the nipple 16 into the spout 20 of the spout pouch 14, avoiding the necessity of the user touching the nipple 16 directly with his or her hands and potentially contaminating it.

Figure 8:
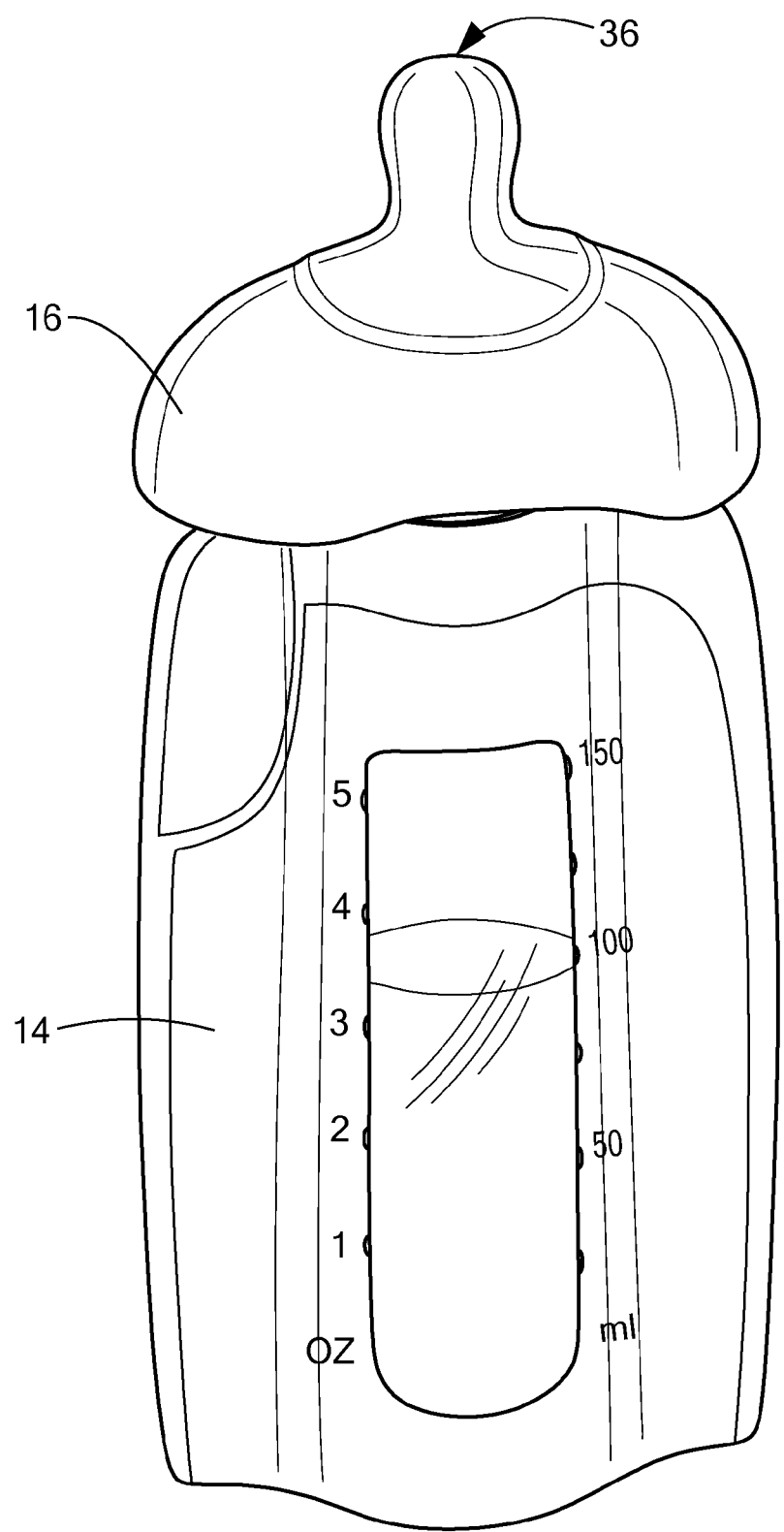
FIG. 8 is a perspective view showing the nipple assembled to the spout pouch, for the purpose of feeding an infant according to embodiments of the present invention.

FIG. 8 is a perspective view showing the nipple 16 assembled to the spout pouch 14, for the purpose of feeding an infant according to embodiments of the present invention. This figure shows the nipple 16 pushed into the spout 20 of the spout pouch 14. In one embodiment, the nipple 16 is pushed into the spout 20 of the spout pouch 14, and an infant could be fed directly from the spout pouch 14. In one embodiment, liquids contained within the spout pouch 14 would flow through the spout 20 and nipple 16, through an orifice 36 in the nipple 16 (described in more detail below in FIGS. 15a-15d), into the infant's mouth. In one embodiment, the spout pouch 14 may be held in a holder 12 (described in more detail in FIGS. 10a-11b). In yet another embodiment, the spout pouch 14 may be held in a holder 12, and a nipple cover 18 may be used to cover the nipple 16 to protect it from contamination (as described above in FIG. 7). In one embodiment, the nipple 16 may be coupled to the spout 20 of the spout pouch 14 by any of a threaded connection, a friction fit, a snap fit, a magnetic coupling, a connection that requires a twisting action, or other type of connection. In one embodiment, the nipple (including a liquid-tight connector for connection to the spout 20) is made of a single piece of material. In other embodiments, the nipple and its connector may be made of multiple components (as described in more detail below in FIGS. 19a-19b).

Figure 9:
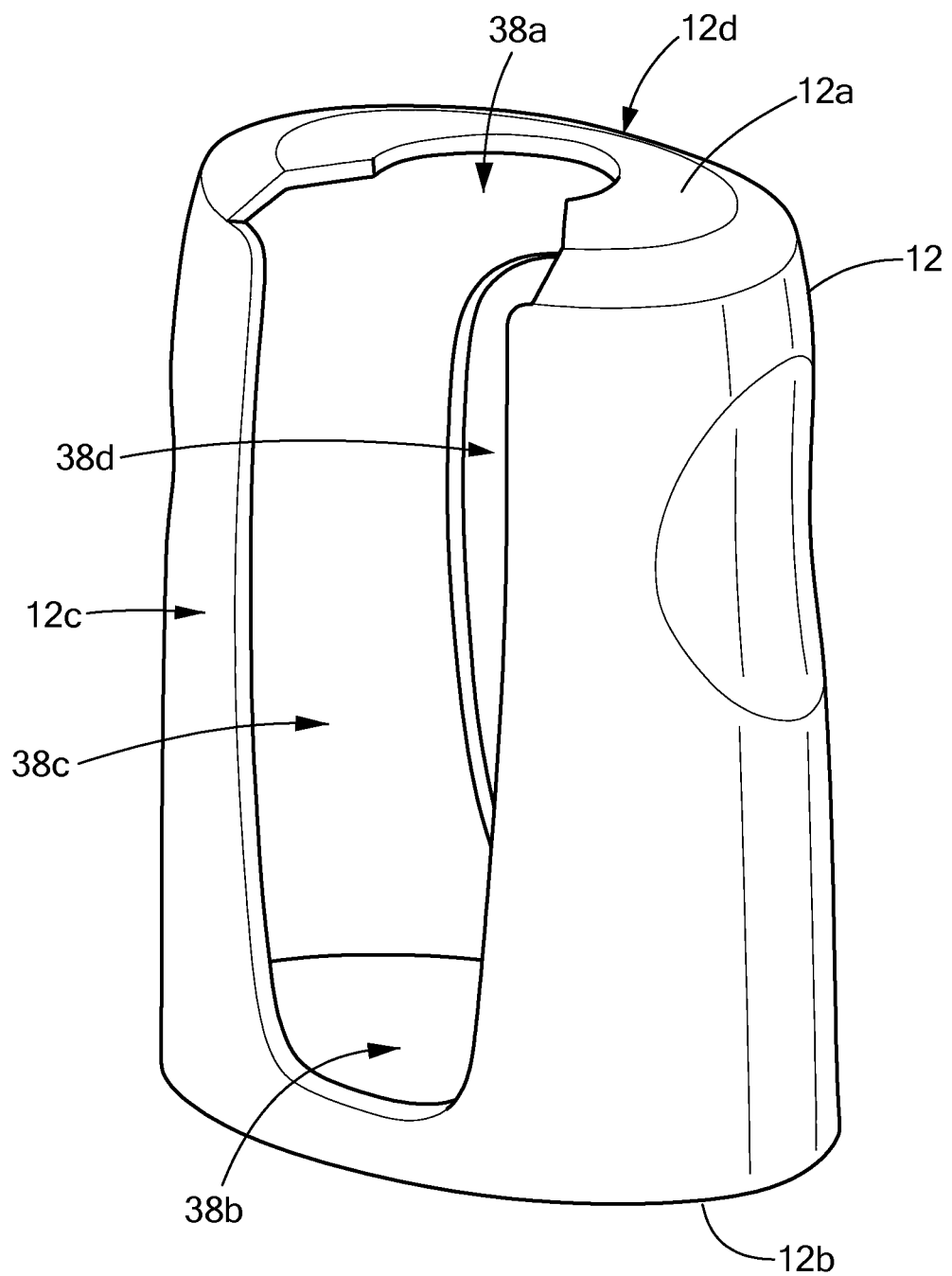
FIG. 9 is a perspective view of an exemplary holder for a spout pouch according to embodiments of the present invention.

FIG. 9 is a perspective view of one embodiment of a holder 12 for a spout pouch 14 according to embodiments of the present invention. The holder 12 may be a thin-walled plastic shell, with openings on the top 12a, bottom 12b, front 12c, and/or back 12d of the holder. The opening 38a on the top 12a of the holder may be a C-shaped opening that is configured to receive a portion of the spout 20 of the spout pouch 14, so as to couple the spout 20 to the holder 12 by way of a snap fit configuration, although other shaped top openings may also be used. The snap fit configuration will be described in more detail below. In addition, the holder 12 may have an opening 38b in the bottom 12b of the holder 12, an opening 38c in the front 12c of the holder 12, and/or an opening 38d in the back 12d of the holder 12. These openings can be used for any of inserting the pouch 14 into the holder; squeezing the pouch 14 to push gas, liquid, or food out of the pouch 14; or for gripping the holder 12. For example, two large openings 38c, 38d on the front 12c and back 12d of the holder 12 may provide gripping surfaces for a two-handed grip for an infant, as well as providing multiple other gripping options for adults or infants.

Figure 10A:
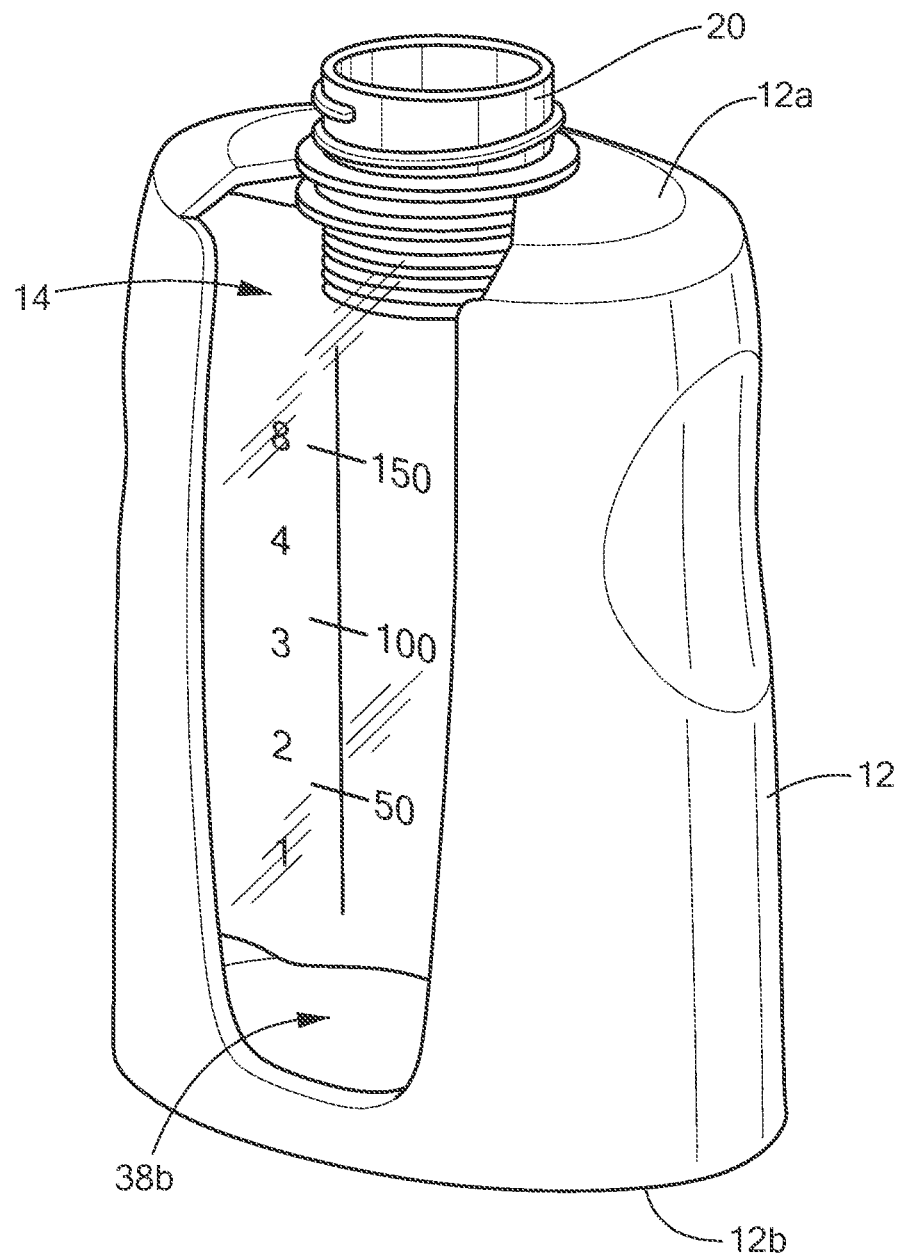
FIG. 10a is a perspective view and FIG. 10b is a rear view showing the spout pouch assembled to the holder according to embodiments of the present invention.
Figure 10B:
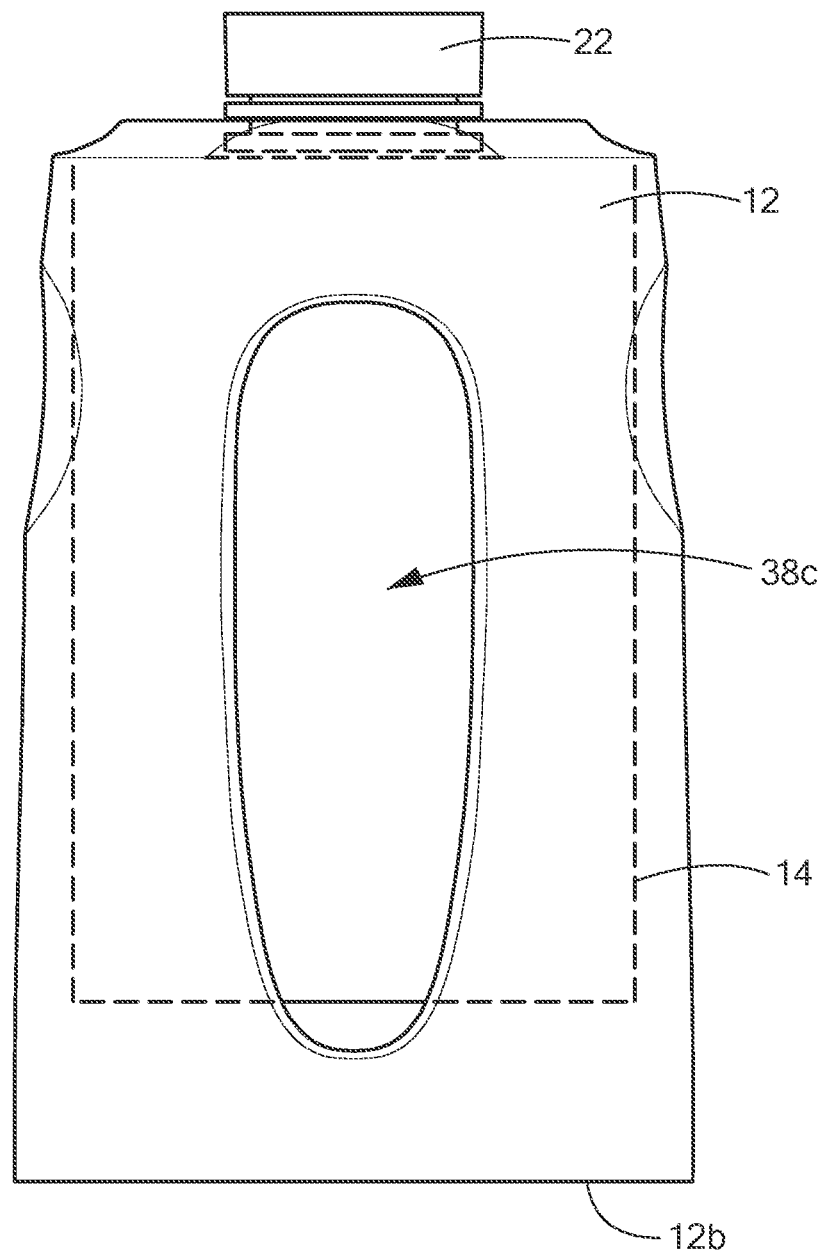

FIGS. 10a and 10b show the spout pouch 14 assembled to the holder 12 using a snap fit configuration between the spout 20 and the opening 38a in the top 12a of the holder 12. During assembly, the spout 20 may be inserted into the top opening 12a of the holder 12 in a snap fit configuration. The opening 38a may be C-shaped and may have a narrow "mouth" through which a portion of the spout 20 must be passed. The width of the C-shaped opening 38a is smaller than a dimension of a portion of the spout 20, such that the passing of the portion of the spout through the "mouth" of the C-shaped opening causes the spout 20 to be substantially held in place. In other embodiments, a portion of the spout 20 may simply be forced into a portion of the holder 12, causing the spout 20 to be coupled to the holder 12 by friction. In another embodiment, the spout 20 may be coupled to the holder 12 by a threaded connection. In other embodiments, the spout 20 may be coupled to the holder by any of a friction fit, a snap fit, a magnetic coupling, a connection that requires a twisting action, or other type of connection. In other embodiments, the holder 12 may have thicker walls, walls of non-uniform thickness, and/or may be constructed of flexible materials.

As shown in FIG. 10b, the holder 12 may rest on a flat surface without the pouch 14 contacting that surface, as a result of the pouch 14 being substantially shorter than holder. As mentioned previously, the cap 22 may be placed on the spout 20 of the spout pouch 14. The cap 22 may be threaded onto the spout 20 of the spout pouch 14, forming a liquid-tight seal between the cap 22 and the spout 20. As shown, the spout 20 and spout pouch 14 can be coupled to the holder 12 with the cap 22 of the spout pouch 14 coupled to the spout 20, so as to ensure the contents of the pouch 14 are not spilled during installation of the pouch 14 into the holder 12.

Figure 11A:
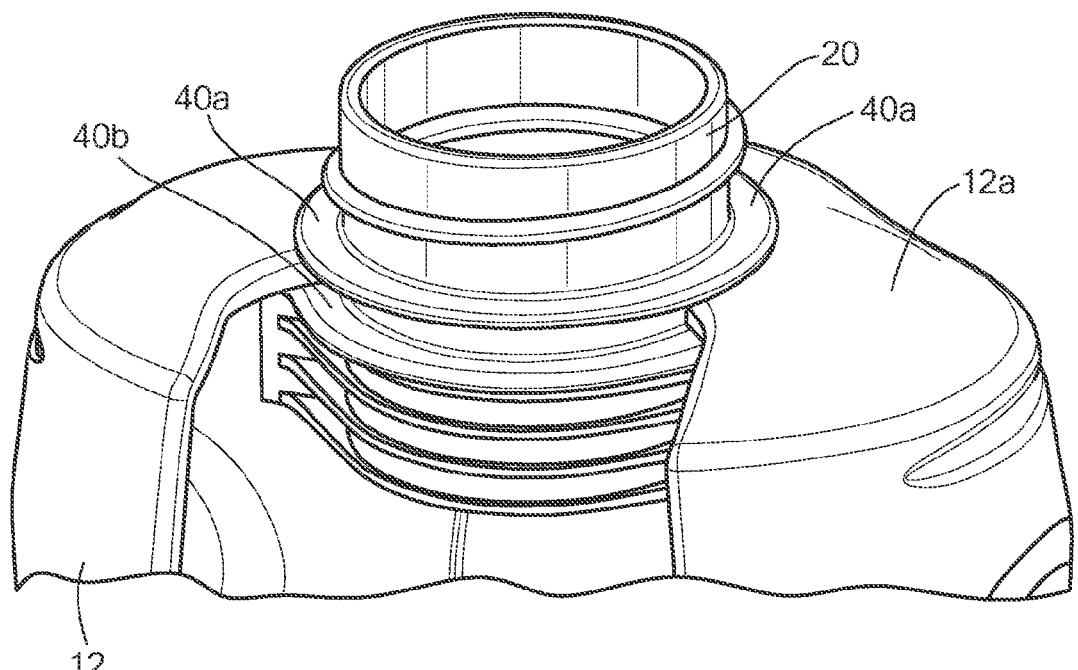
FIG. 11a is a close-up, perspective view
Figure 11B:
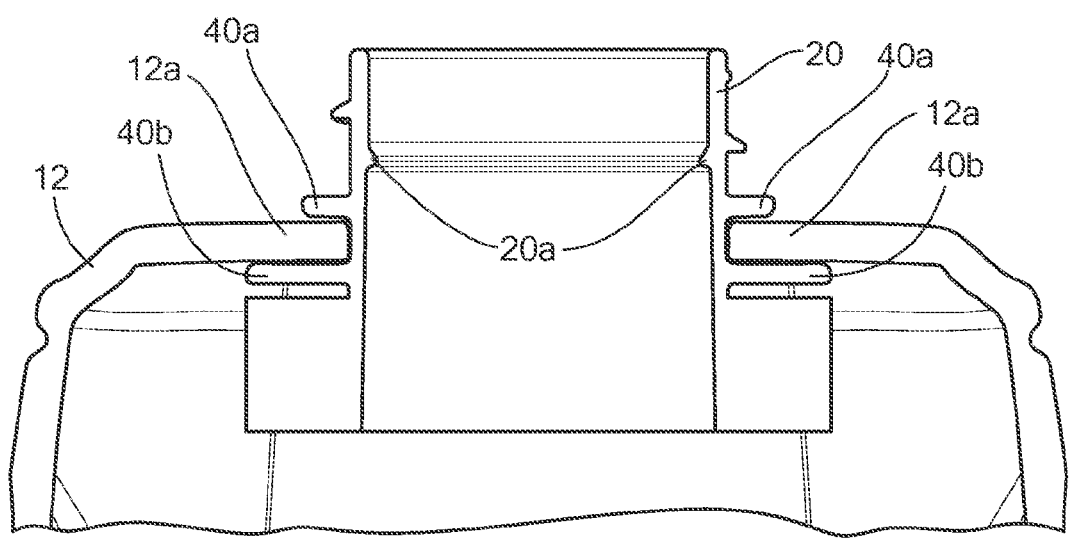
FIG. 11b is a cross-sectional view showing a snap fit between the spout of the spout pouch and the holder according to embodiments of the present invention.

As shown in more detail in FIGS. 11a and 11b, the coupling between the spout 20 and the holder 12 may be a snap fit as described above. The spout 20 of the spout pouch 14 may have two flanges—an upper flange 40a and a lower flange 40b. The two flanges are spaced apart, such that, when the spout 20 is snapped into the opening 38a in the holder, the upper flange 40a is above a top surface of the top 12a of the holder 12, and the lower flange 40b is below the top surface of the holder 12. With this type of configuration, the flanges 40a, 40b prevent movement of the spout 20 and pouch 14 within the holder 14, along the longitudinal axis of the spout 20. The spout 20 may also include a feature 20a, such as a circumferential ridge, rib, boss, groove, or step, inside (or outside) the spout 20 with which the connector 24 may engage and help hold the nipple 16 in place once it is coupled to the spout 20.

Figure 12:
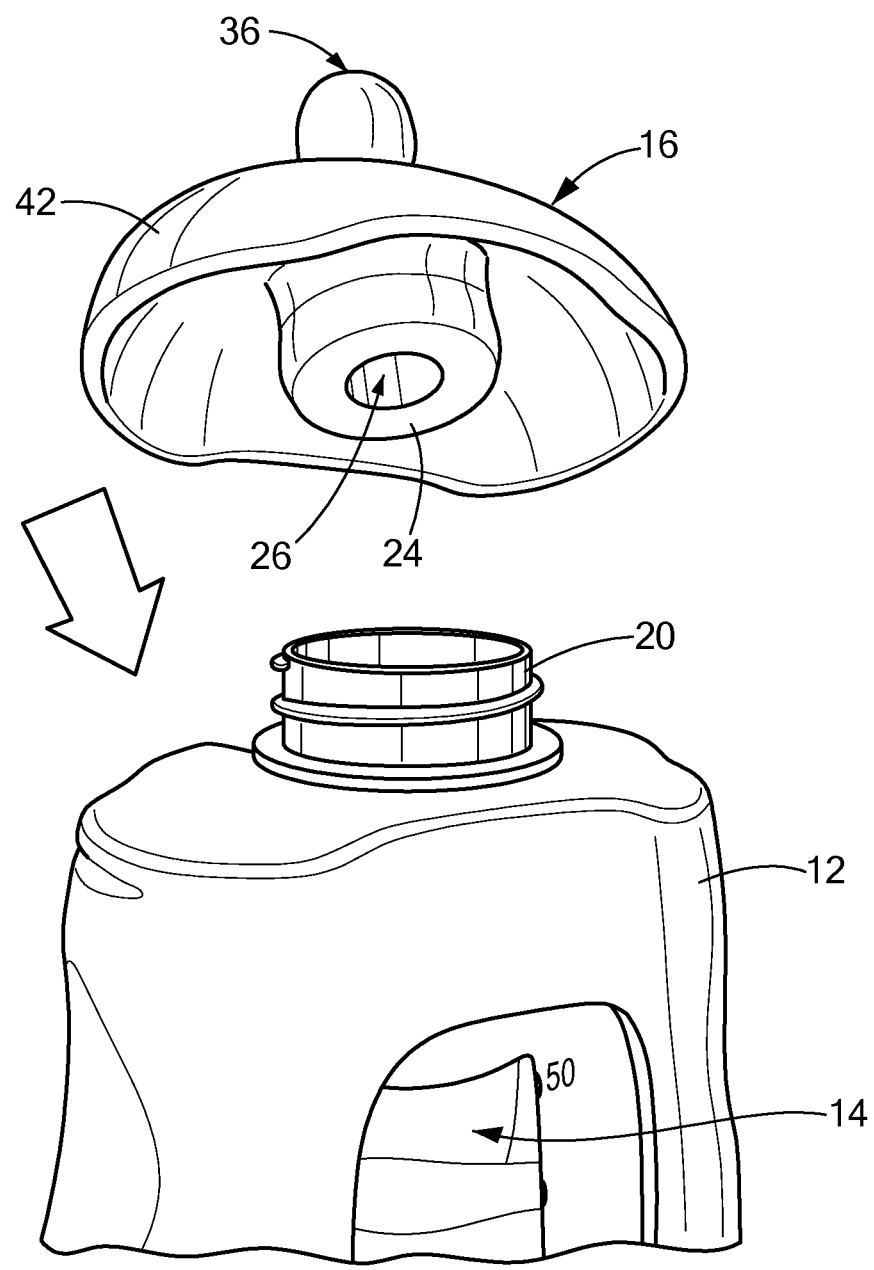
FIG. 12 is a perspective view showing the assembly of the nipple onto the spout pouch, the spout pouch being held in the holder according to embodiments of the present invention.
Figure 13:
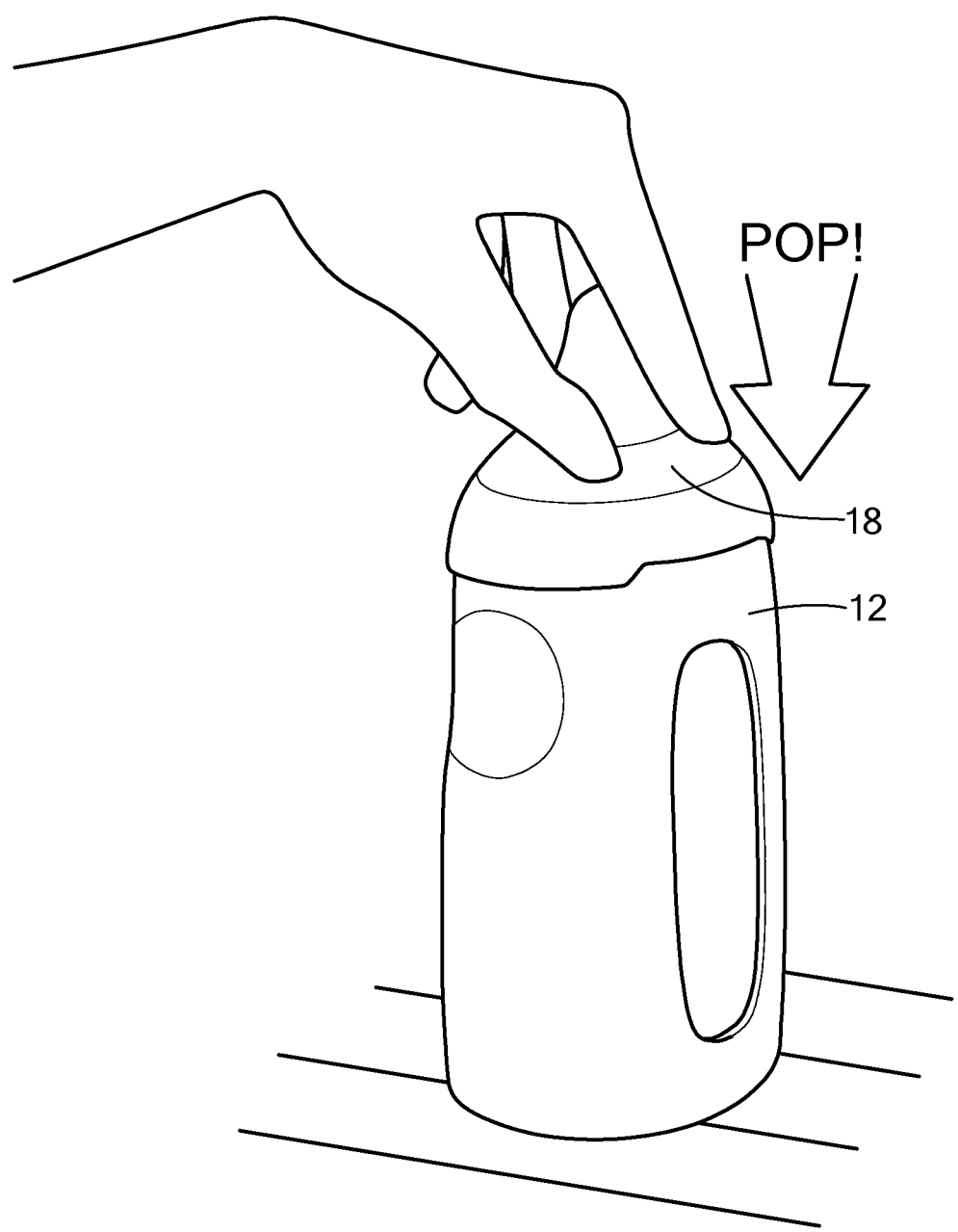
FIG. 13 is a perspective view showing the top of the nipple case being used to push the nipple into the spout pouch according to embodiments of the present invention.
Figure 14:
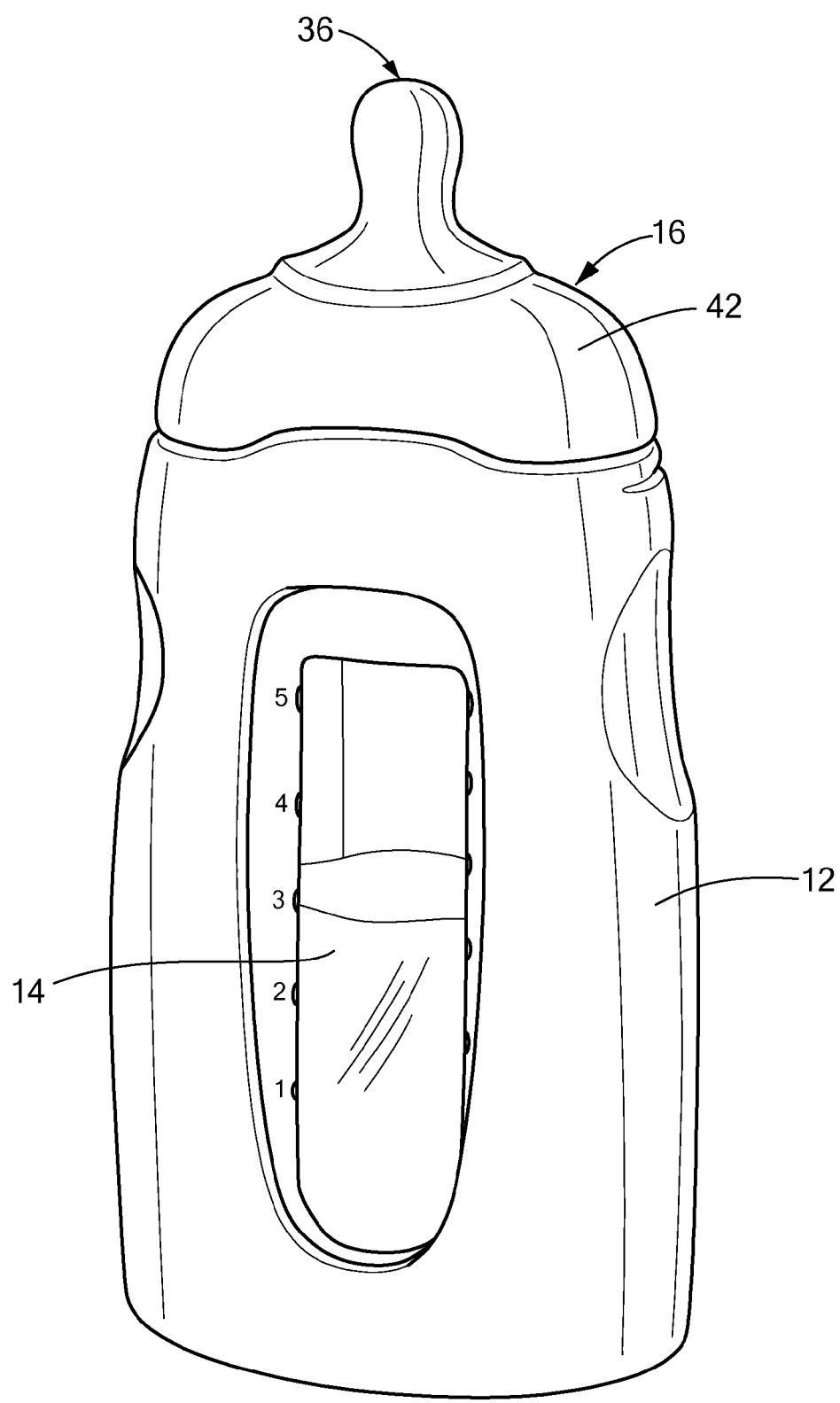
FIG. 14 is a perspective view of an assembled spout pouch, nipple, and holder according to embodiments of the present invention.

FIGS. 12 through 14 show the assembly of the nipple 16 onto the spout pouch 14, the spout pouch 14 being held in the holder 12. As described in more detail in FIGS. 15a-15d, the nipple 16 may have a skirt 42 with a generally oblong shape. On the underside of the nipple 16, there may be a connector 24 with an axial bore 26, as shown in FIG. 12. During the nipple insertion process, the connector 24 gets pushed into the spout 20 of the spout pouch 14, forming a liquid-tight seal between the outer surface (or set of surfaces) of the connector 24 and the inner surface (or set of surfaces) of the spout 20 or of a feature connected to the spout 20. The axial bore 26 passes from the end of the connector 24 through to the tip of the nipple 16, where it meets the nipple orifice 36. Once the nipple 16 is pushed into place onto the spout 20, the contents of the pouch 14 can pass through the axial bore 26 of the nipple 16, through the orifice 36, and into the mouth of an infant.

As shown in FIG. 13, the nipple cover 18 may be used to push the nipple 16 into the spout pouch 14. In this case, the nipple cover 18 is used as a tool to push the nipple 16 into place, as the connector 24 is forced into the spout 20 of the spout pouch 14, while also protecting the nipple 16 from contamination during the nipple insertion process. Once the nipple 16 is securely in place (e.g., once the connector 24 is securely in place inside the spout 20 of the spout pouch 14), the nipple cover 18 may be lifted off, leaving the nipple 16 in place, securely coupled to the spout 20 and forming a liquid-tight seal with the spout 20. As such, the user's hands never come in direct contact with the nipple 16.

FIG. 14 shows the nipple 16 fully assembled onto the spout 20 of the spout pouch 14 with the spout pouch 14 assembled to the holder 12. As shown, the skirt 42 of the nipple 16 contacts a top surface of the top 12a of the holder once the connector 24 is coupled to the spout 20 of the spout pouch 14. In one embodiment, the skirt 42 of the nipple 16 and the holder 12 are both generally oblong in cross-sectional shape. The oblong shape of the skirt 42 of the nipple 16 helps to create a more ergonomic shape, and a better seal between the nipple 16 and an infant's mouth. In other embodiments, the cross-sectional shape of the skirt 42 of the nipple 16 and of the holder 12 may be round, oval, or other polygonal shape with or without rounded corners.

FIGS. 15a-15d and 16 show a one-piece feeding nipple having an oblong shape that is designed to be pushed into a spout pouch 14 for the purpose of feeding an infant. As shown, the nipple 16 includes a connector 24 having a connector region 24a which is designed to be pushed into, and engage, the spout 20 of the spout pouch 14 to form a liquid-tight seal without the need for any additional rings or other hardware. The nipple 16 also includes a tip region 44, which is meant to be inserted into the mouth of an infant. In addition, the nipple 16 includes a skirt 42 having a lower region 46 that generally surrounds the connector 24 and connector region 24a and an abutment region 48 that abuts the tip region 44, such that the infant's lips meet the nipple 16 near the transition from the abutment region 48 to the lower region 46. The skirt 42 may having a bottom end 42a that has a generally oblong shape, with the oblong shape having a long axis (along line L in FIG. 15d) and a short axis (along line S in FIG. 15d). The abutment region 48 may have a textured surface, and there may be a shoulder 50 between the abutment region 48 and the lower region 46.

For example, there may be a slight "step" or raised area of material near where the tip region 44 connects to the skirt 42 along the abutment region 48. The shoulder 50 may be positioned at the approximate location of an infant's lips during feeding from the nipple. The shoulder 50 may extend around the circumference of the nipple 16. This step may be advantageously positioned slightly outside the area where the connector 24 meets the underside of the skirt 42. The shoulder 50 may be designed to provide an ergonomically or functionally favorable resting position for an infant's lips during feeding. The shoulder 50 may also help provide a better seal between an infant's lips and the nipple 16. The abutment region 48 may have a stiffness greater than the stiffness of the lower region 46, (e.g., due to a greater thickness in the abutment region) in order to facilitate better latching or an ergonomically or functionally superior coupling between an infant's mouth and the nipple 16 toward the lower region 46. For example, there may be a decrease in thickness of the material in the lower region 46 where an infant's lips may be positioned during feeding. Such a decrease in thickness may cause a decrease in stiffness of the material at that location. This decrease in stiffness, or increase in apparent softness may help provide an ergonomically or functionally favorable resting position for an infant's lips during feeding. This decrease in stiffness may also help provide a better seal between an infant's lips and the nipple. In some embodiments, the shoulder 50 and the decrease in thickness described above may be combined. In some embodiments, the skirt 42 of the nipple 16 may be round, rather than oblong, in shape. In one embodiment, the nipple 16 may be advantageously made of a single piece of material. This has many advantages, primarily the simplicity of only having one piece to handle, store, clean, and install.

Figure 15A:
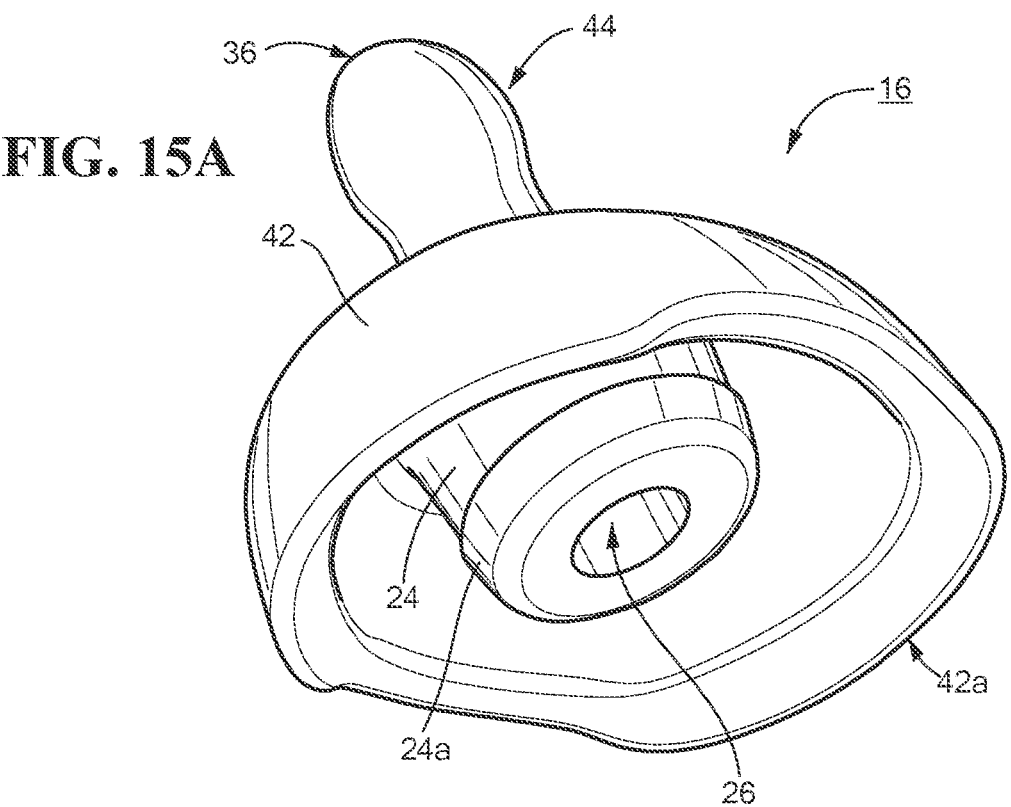
FIGS. 15a-15d show a one-piece feeding nipple having an oblong shape according to embodiments of the present invention.
Figure 15B:
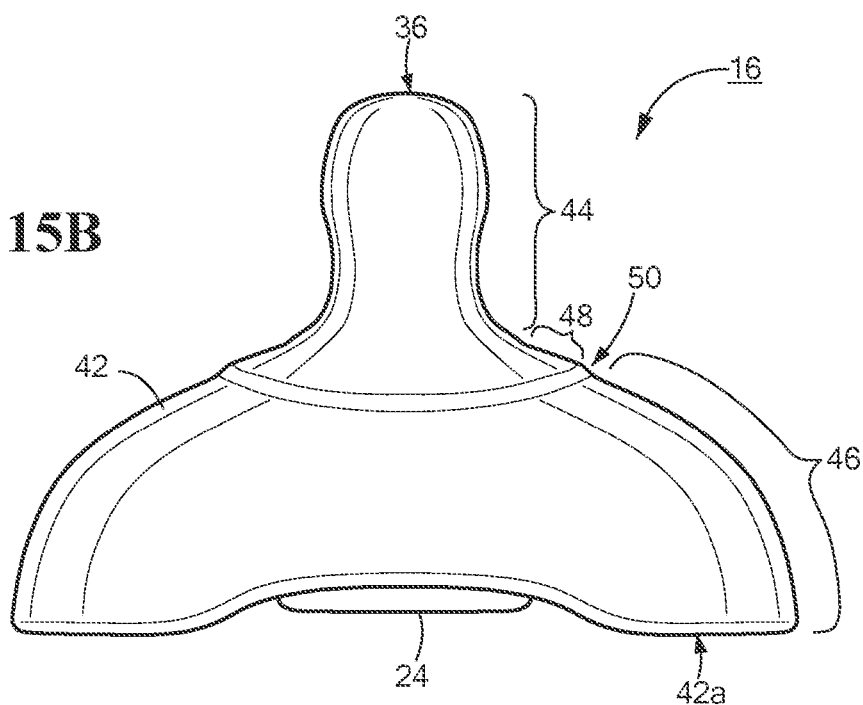
Figure 15C:
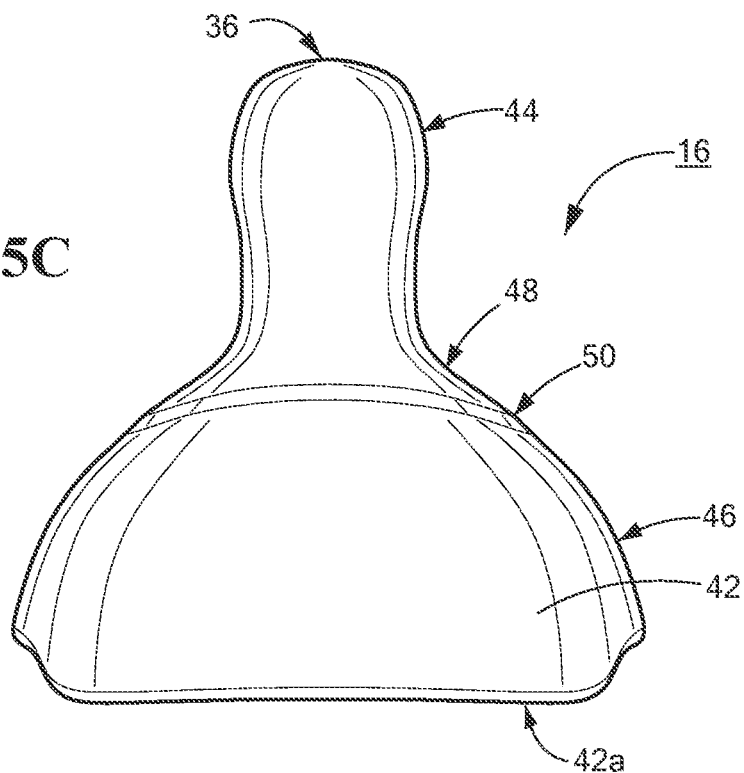
Figure 15D:
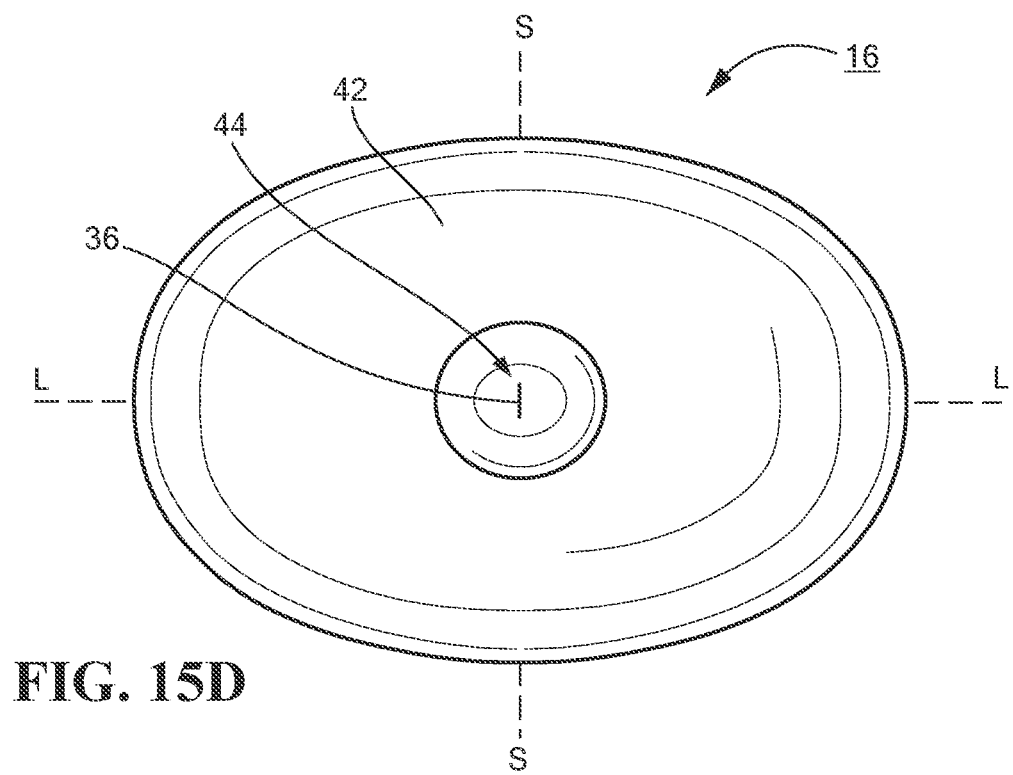

FIG. 15b shows a front view of the long axis of the oblong shape of the skirt 42 of the nipple 16. FIG. 15c shows a side view of the short axis of the oblong skirt 42 of the nipple 16. FIG. 15d shows a top view of a one-piece feeding nipple with an orifice 36 at the tip of the nipple 16. The orifice 36 may be in the shape of a slit, through which the pouch 14 contents pass into the infant's mouth. In one embodiment, the slit may be oriented transverse to the long axis of the oblong shape of the skirt 42 of the nipple, such as shown in FIG. 15d. The slit length defines an axis, "the slit axis", along the short axis of the skirt 42, that is transverse to the long axis of the oblong nipple skirt 42. When the tip region 44 of the nipple 16 is compressed in the direction of the slit axis, the slit may open, allowing the flow of liquids, pastes, gels, or food through the slit. The slit axis is oriented such that it will run generally from top to bottom in an infant's mouth, meaning that natural up and down massaging motion of the infant's tongue can cause deformation along the slit axis, which can in turn cause the slit to open, allowing the contents of the pouch 14 to flow through the slit. Additionally, suction from the infant's mouth may cause or increase the flow of the pouch contents through the slit. In other embodiments, the orifice in the tip region of the nipple may be a hole. A slit in the nipple may be a straight line, as described above, or it may be curved. A curved slit could be used to create different flow patterns or different flows based on different types of deformation of the tip region of the nipple.

Figure 16:
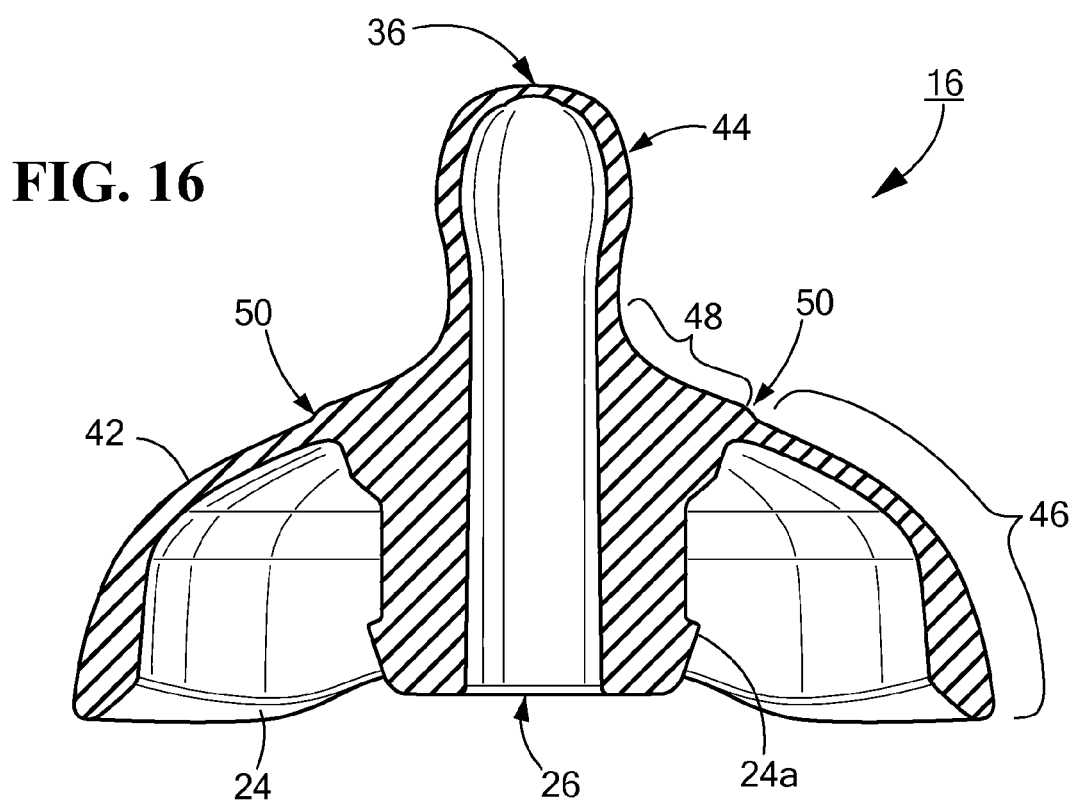
FIG. 16 is a cross-sectional view of a one-piece feeding nipple having an oblong shape that is designed to be pushed into a spout pouch for the purpose of feeding an infant according to embodiments of the present invention. This figure shows in detail the connector, which gets pushed into the spout of the spout pouch. It also shows the flange on the connector, which can engage with a feature in the spout of the spout pouch, to help hold the nipple in place.

FIG. 16 shows a cross-sectional view of a one-piece feeding nipple 16. As shown, the connector 24 may include a connector region 24a, which can engage with a feature 20a in the spout 20 of the spout pouch 14, to help hold the nipple 16 in place (such as shown and discussed in FIG. 11b). The connector region 24a may be a flange. In one embodiment, the nipple 16, including the connector 24, the tip region 44 and the skirt 42, may be made of a soft, compressible material, such as silicone or rubber. In one embodiment, the connector 24 may be frustro-conical in shape, with a round bore 26, and its outer diameter may be slightly larger than an inside diameter of the spout 20 of the spout pouch 14. When the connector 24 is pushed into position inside the spout 20, the connector 24 deforms and pushes out against an inner surface of the spout 20. As such, the connector 24 forms a liquid-tight seal with the spout 20 of the spout pouch 14, much in the same way that a cork or stopper forms a liquid-tight seal with the inner surface of a mouth of a bottle. Alternatively, the connector 24 may fit on an outside surface of an opening in the spout 20 in order to form a liquid-tight seal with the spout 20. For example, the connector 24 may engage one or both of an internal surface of the spout 20 and an external surface of the spout 20. In some embodiments, the spout 20 of the spout pouch 14 may be made of a relatively soft, compressible material, such that the spout 20 deforms more than the connector 24 when the connector 24 is pushed into place. In one embodiment, there is a feature (e.g., a flange) that extends around the circumference of the connector 24 in the connector region 24a. The spout 20 may include a feature 20a, such as a circumferential ridge, boss, or groove, (e.g., as shown in FIG. 11b) inside the spout 20 of the spout pouch 14 with which this connector feature engages to help hold the nipple 16 in place once it is coupled to the spout 20. In one embodiment, this feature may be a groove, a step, or other feature that could engage with a feature in or on the spout 20 of the spout pouch 14 to help hold the nipple 16 in place inside, or otherwise coupled to, the spout 20. FIG. 16 also shows the axial bore 26, which is open at the bottom end of the connector, and extends through the nipple 16. The axial bore 26 is coupled to the orifice 36 at the tip of the nipple 16. As such, pouch 14 contents can flow through the axial bore 26, through the orifice 36, and into the mouth of an infant.

Figure 17:
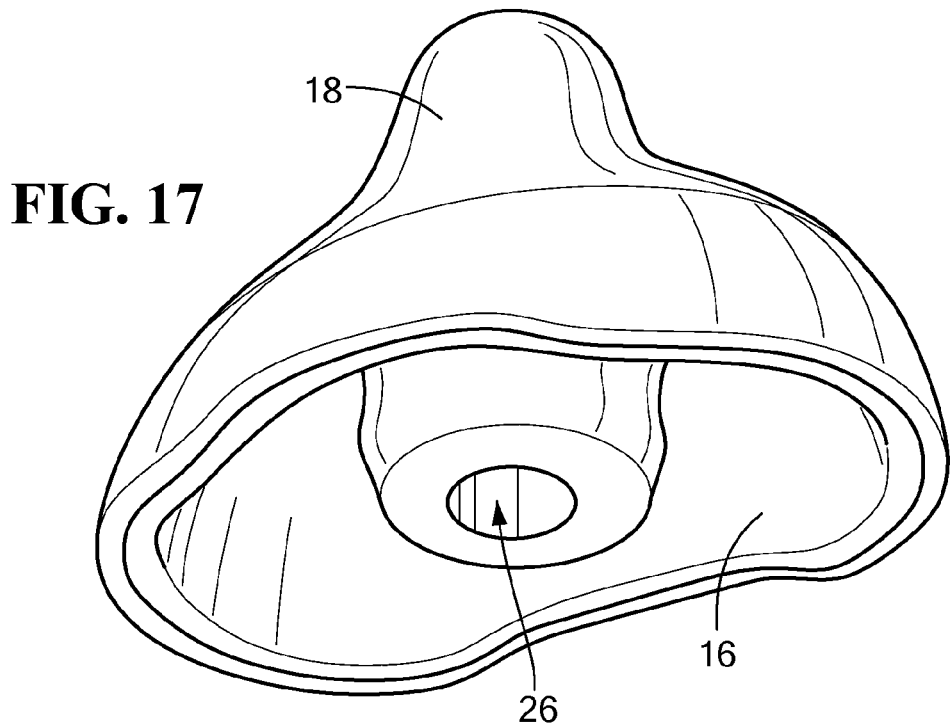
FIG. 17 is a perspective, bottom view showing the nipple inside the nipple cover according to embodiments of the present invention.

FIG. 17 shows the nipple 16 inside the nipple cover 18. As stated above, a user may grip the top of the nipple cover 18, never touching the nipple itself, and use the top of the nipple cover 18 as a tool to push the nipple 16 into place in or on the spout 20 of the spout pouch 14.

Figure 18:
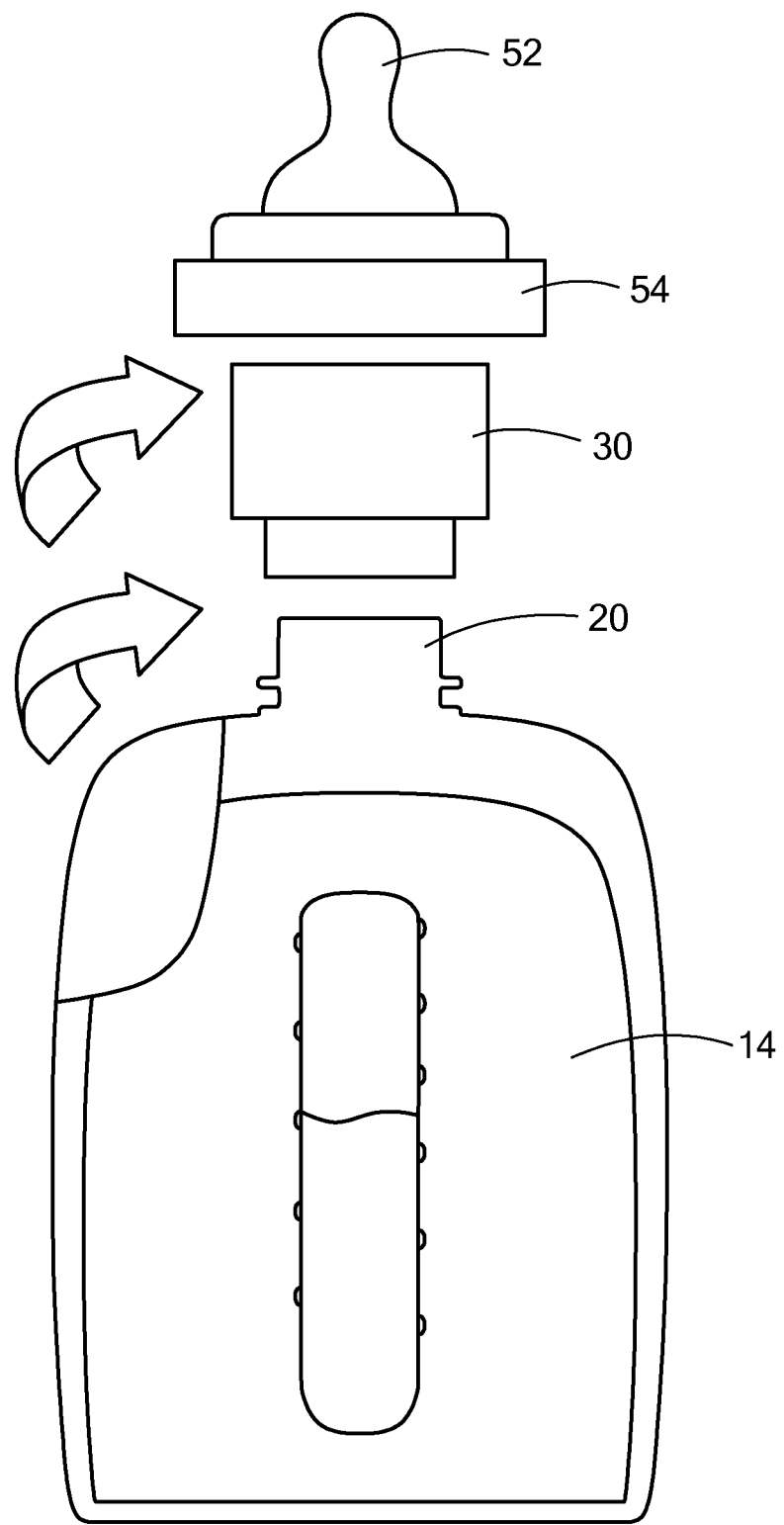
FIG. 18 is an exploded view of a spout pouch with an adapter for fitting a conventional feeding nipple and ring onto the spout pouch according to embodiments of the present invention.

FIG. 18 shows a spout pouch 14 with an adapter 30 for fitting a conventional feeding nipple 52 and attachment ring 54 onto the spout pouch 14 according to embodiments of the present invention.

Figure 19A:
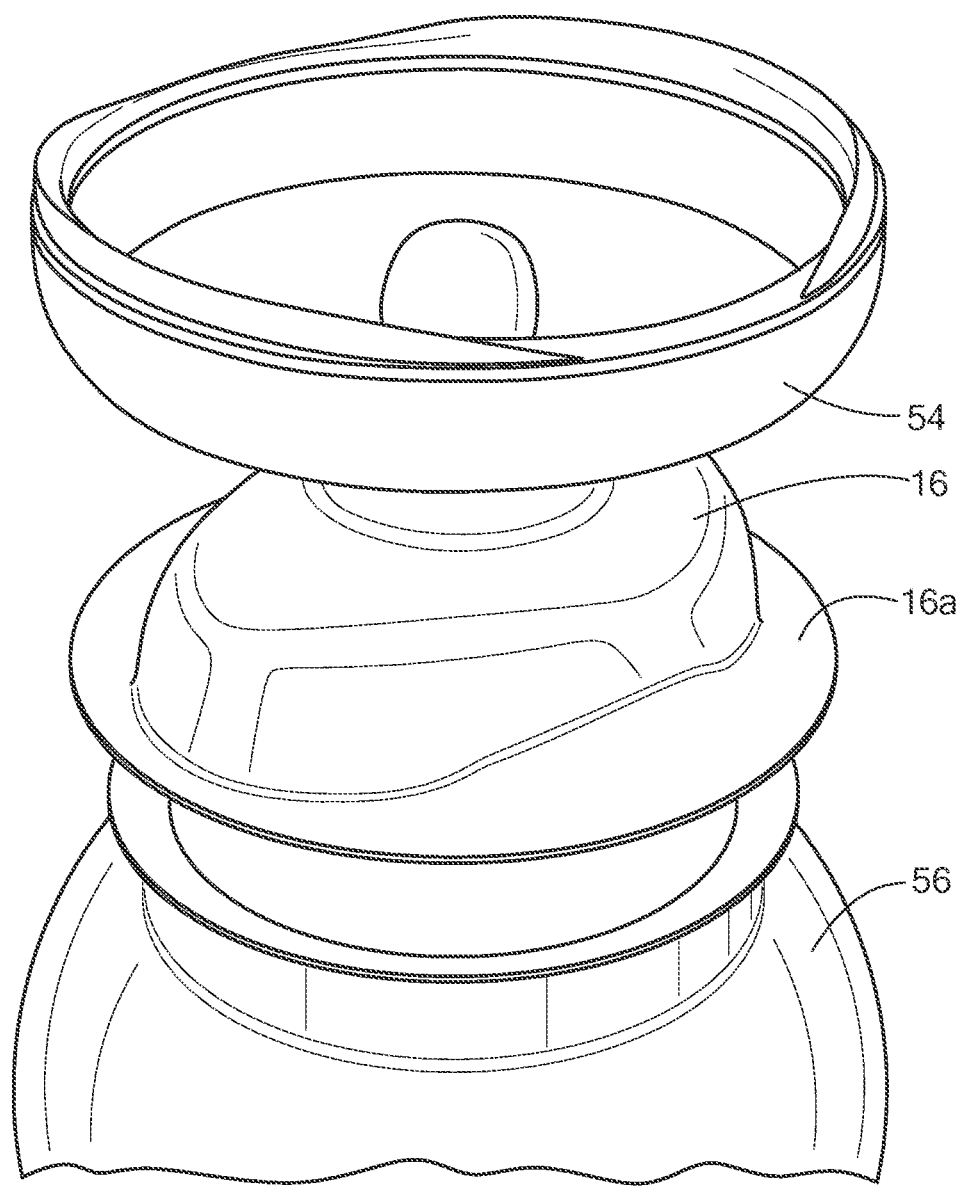
FIGS. 19a and 19b show an exploded view and an assembled view, respectively, of an oblong nipple having a securing flange secured onto a conventional bottle according to embodiments of the present invention.
Figure 19B:
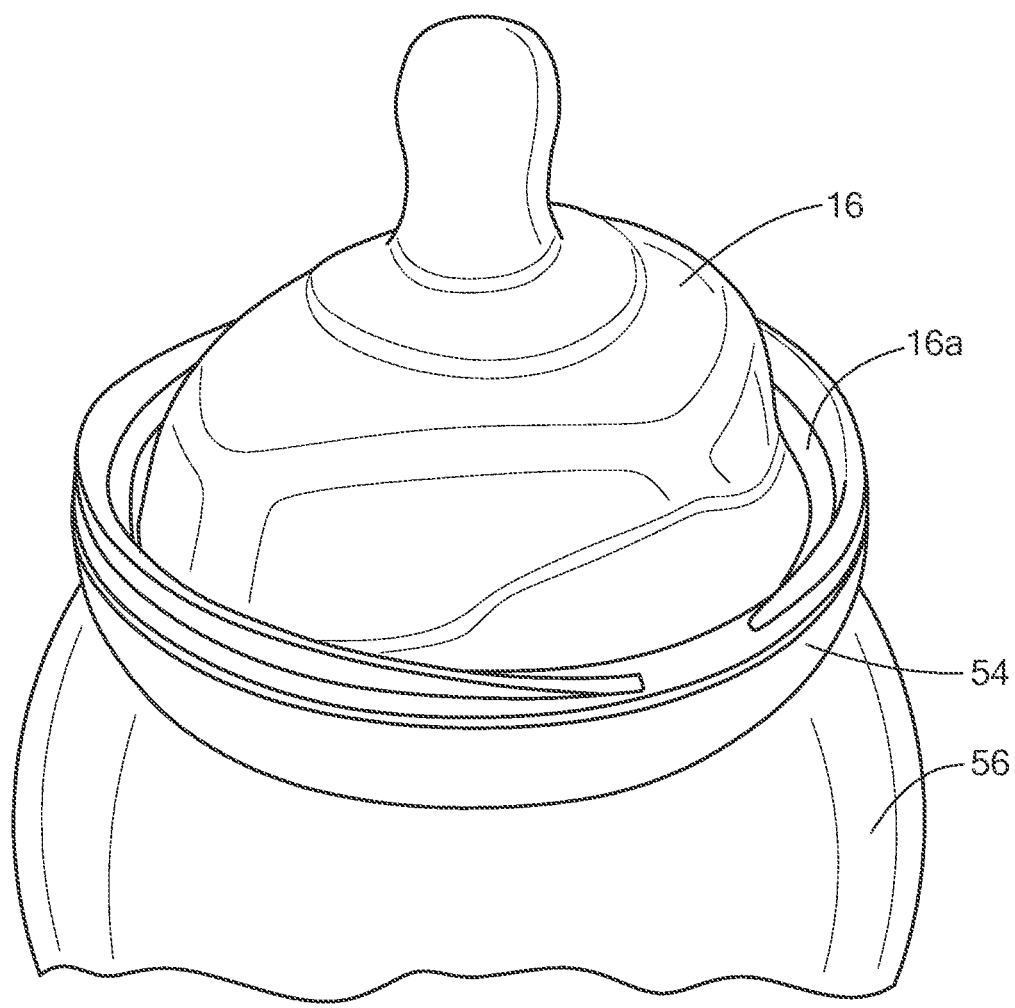

FIGS. 19a and 19b show an oblong nipple 16 having a securing flange 16a at the bottom of the skirt 42 that may be secured onto a conventional bottle 56 using a standard attachment ring 54, e.g., lock ring, all in accordance with embodiments of the present invention. As shown, the attachment ring 54 may attach to the top of a bottle 56 using a threaded connection. The nipple 16 may have a securing flange 16a that connects to the bottom of the skirt 42 and extends outward, such that the flange 16a is pressed against a surface of the bottle when the attachment ring 54 is assembled to the bottle 56. In one embodiment, the securing flange 16a forms a liquid-tight seal with a surface of the bottle 56, when the attachment ring 54 is tightened into place. In one embodiment, the skirt 42 of the nipple 16 that contacts the infant's mouth may be oblong in shape. The securing flange 16a may extend outward from the base of the skirt region to form a circle at its outer perimeter. For example, the nipple 16 includes of a tip region 44 connected to a generally oblong skirt 42, which is connected to a thin securing flange 16a that is generally circular at its outer edges.

Figure 20A:
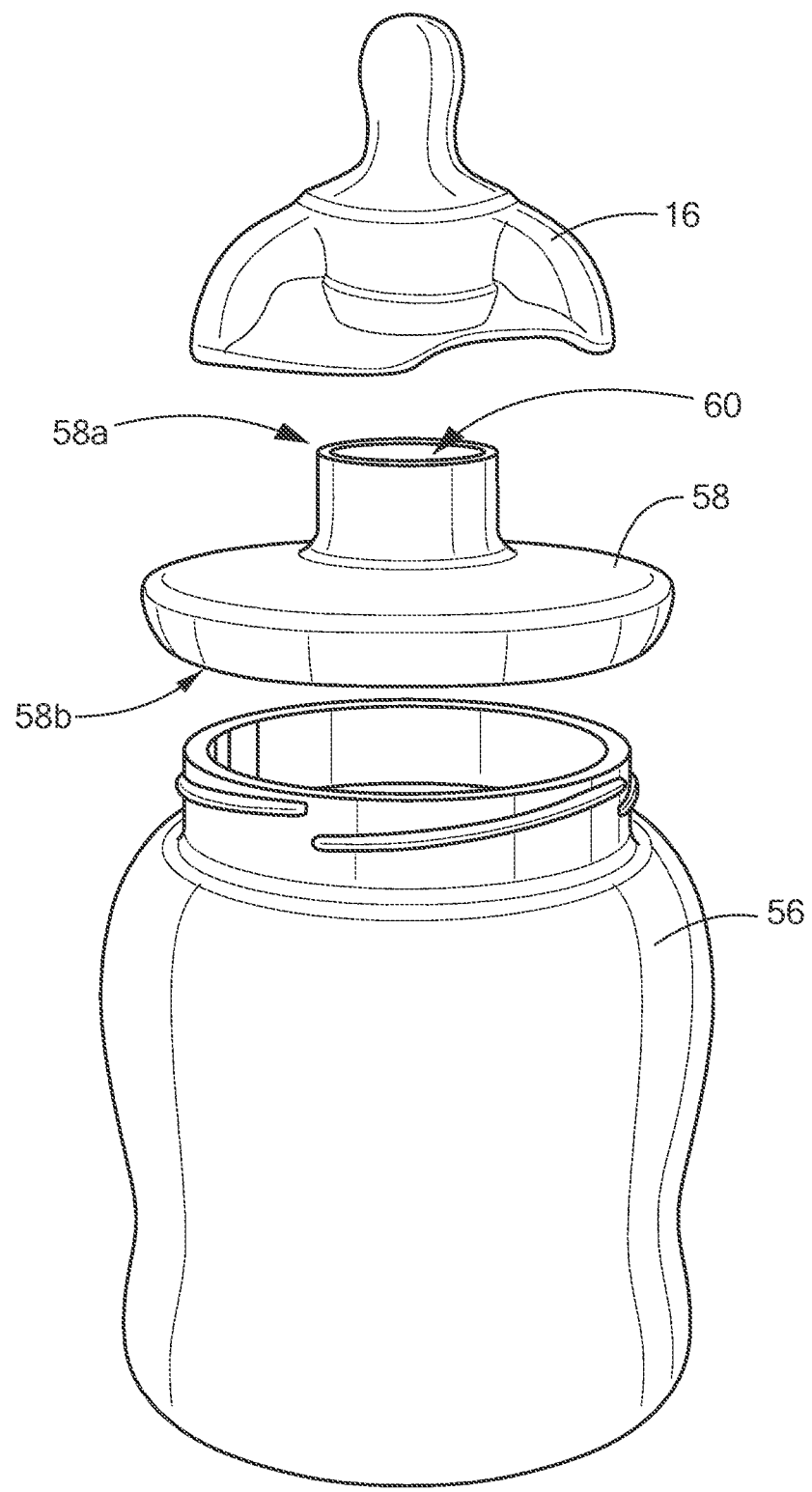
FIGS. 20a and 20b show an exploded view and an assembled view, respectively, of an oblong nipple secured onto a conventional bottle using a nipple adapter according to embodiments of the present invention.
Figure 20B:
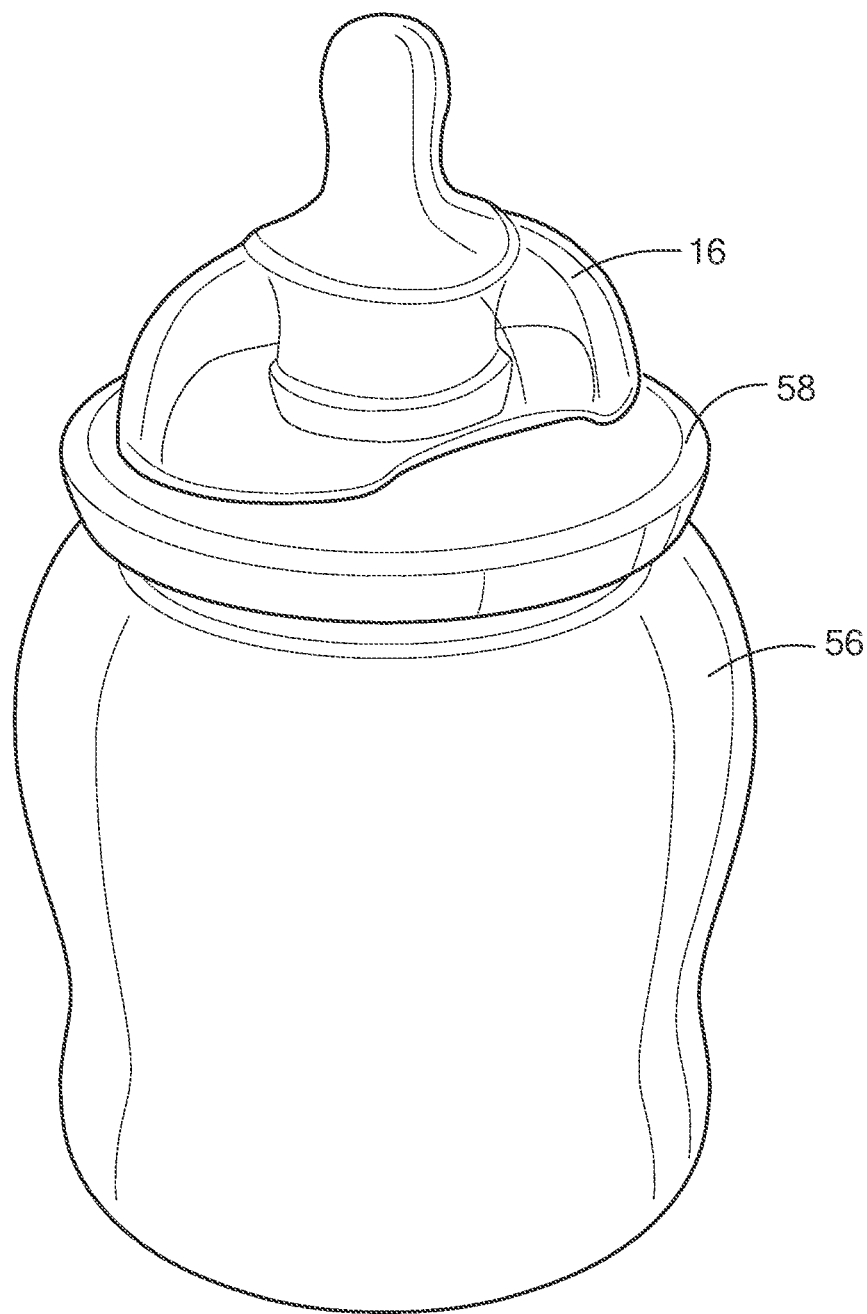

FIGS. 20a and 20b show an oblong nipple 16 having a connector 24 that is secured onto a conventional bottle 56 using a nipple adapter 58 according to embodiments of the present invention. As shown, the nipple adapter 58 couples the nipple 16 to a container for feeding an infant. The nipple adapter 58 has at least one generally cylindrical opening 60 through which liquid flows during feeding. The nipple adapter 58 includes a first end 58a and second end 58b. The first end 58a is configured to be coupled to a nipple 16, and the second end 58b is configured to be coupled to an infant feeding container, e.g., conventional bottle 56. The nipple adapter 58 may contain a spout-like feature on the first end 58a, with an opening configured to receive a connector 24 on the bottom of a nipple 16. On the second end 58b of the nipple adapter 58, there are threads (not shown) for coupling the nipple adapter 58 to a container 56 for feeding an infant. Different adapters 58 of this sort will allow connection of this type of nipple 16 to a wide range of different types of infant feeding containers 56. In one embodiment, the first end 58a of the nipple adapter 58 has an opening configured to receive a connector 24 of the type described above, while the second end 58b of the nipple adapter 58 has an internally threaded connection for coupling with a threaded baby bottle 56. As such, the second end 58b of nipple adapter 58 threads onto a baby bottle 56, and the nipple 16 with connector 24 can be pushed into the opening on the first end 58a of the nipple adapter 58, as described previously above. The first end 58a of the nipple adapter 58 may have internal features as described previously for engaging features on the connector 24, to help hold the nipple in place relative to the nipple adapter 58. A wide variety of bottle types exist, so there may be several different types of connections and threads that can be used on the second end 58b of the nipple adapter 58 for coupling to feeding bottles 56. There may be external threads on the first end 58a of the nipple adapter 58, configured to receive a cap 22.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A method of collecting breast milk for feeding to an infant, the method comprising:
providing a spout pouch, the spout pouch having a spout formed integrally with a pouch;
providing a plurality of adapters configured to couple to the spout pouch;
coupling the spout of the spout pouch to a first adapter;
coupling the first adapter to a breast pump;
operating the breast pump to express breast milk into the spout pouch, so that the spout pouch collects the expressed breast milk;
coupling a second adapter to the spout of the spout pouch;
coupling the second adapter to a nipple, so that expressed breast milk flows from the spout pouch to the nipple; and
inserting the spout pouch into a holder, the holder having a top and a body, wherein the top of the holder has an opening configured to laterally receive and removably secure the spout to the holder when the spout is pushed transversely into the opening with a snap fit, and the body is configured to receive at least a portion of the spout pouch.

2. A method according to claim 1, wherein the first adapter has a first threaded end configured to mate with threads on the spout and a second threaded end configured to mate with threads on the breast pump.

3. A method according to claim 1, wherein the opening in the holder is C-shaped.

4. A method according to claim 1, wherein an entrance to the opening in the holder has a width that is smaller than a width of a portion of an outer surface of the spout, such that the portion of the is out is held securely in place in the opening after the portion of the spout passes through the entrance of the opening.

5. A method according to claim 1, wherein the second adapter has a first threaded end configured to mate with threads on the spout and a second threaded end configured to mate with threads on the nipple or a nipple component.

6. A method according to claim 1, wherein the opening in the holder includes a mouth and a throat, the opening configured to allow at least a portion of the spout to pass through the mouth and to enable the spout to be pressed into the throat when the spout is secured to the holder.

7. A method according to claim 6, wherein the opening is in the shape of an arc having a constriction, the opening configured to allow a portion of the spout to be forced past the constriction when the spout is secured to the holder.

8. A method according to claim 7, wherein the arc is greater than 180 degrees with a sufficient gap to allow the spout to be forced into the opening.

9. A method of collecting breast milk for feeding to an infant, the method comprising:
- providing a spout pouch, the spout pouch having a spout formed integrally with a pouch;
- coupling the spout of the spout pouch to an adapter;
- coupling the adapter to a breast pump;
- operating the breast pump to express breast milk into the spout pouch, so that the spout pouch collects the expressed breast milk;
- removing the breast pump;
- coupling the adapter to a nipple, so that expressed breast milk flows from the spout pouch to the nipple; and
- inserting the spout pouch into a holder, the holder having a top and a body, wherein the top of the holder has an opening configured to laterally receive and removably secure the spout to the holder when the spout is pushed transversely into the opening with a snap fit, and the body is configured to receive at least a portion of the spout pouch.

10. A method according to claim 9, wherein the adapter has a first threaded end configured to mate with threads on the spout and a second threaded end configured to mate with threads on the breast pump.

11. A method according to claim 9, wherein the opening in the holder is C-shaped.

12. A method according to claim 9, wherein an entrance to the opening in the holder has a width that is smaller than a width of a portion of an outer surface of the spout, such that the portion of the spout is held securely in place in the opening after the portion of the spout passes through the entrance of the opening.

13. A method according to claim 9, wherein the adapter has a first threaded end configured to mate with threads on the spout and a second threaded end configured to mate with threads on the nipple or a nipple component.

14. A method according to claim 9, wherein the opening in the holder includes a mouth and a throat, the opening configured to allow at least a portion of the spout to pass through the mouth and to enable the spout to be pressed into the throat when the spout is secured to the holder.

15. A method according to claim 14, wherein the opening is in the shape of an arc having a constriction, the opening configured to allow a portion of the spout to be forced past the constriction when the spout is secured to the holder.

16. A method according to claim 15, wherein the arc is greater than 180 degrees with a sufficient gap to allow the spout to be forced into the opening.

* * * * *